(12) United States Patent
Jendrisak et al.

(10) Patent No.: US 9,017,970 B2
(45) Date of Patent: Apr. 28, 2015

(54) RNA POLYPHOSPHATASE COMPOSITIONS, KITS, AND USES THEREOF

(75) Inventors: Jerome J. Jendrisak, Madison, WI (US); Ramesh Vaidyanathan, Madison, WI (US); Ronald Meis, Fitchburg, WI (US)

(73) Assignee: CellScript, LLC, Madison, WI (US)

( * ) Notice: Subject to any disclaimer, the term of this patent is extended or adjusted under 35 U.S.C. 154(b) by 823 days.

(21) Appl. No.: 12/990,750

(22) PCT Filed: May 4, 2009

(86) PCT No.: PCT/US2009/042729
§ 371 (c)(1),
(2), (4) Date: Feb. 17, 2012

(87) PCT Pub. No.: WO2009/135214
PCT Pub. Date: Nov. 5, 2009

(65) Prior Publication Data
US 2012/0196278 A1    Aug. 2, 2012

Related U.S. Application Data

(60) Provisional application No. 61/050,041, filed on May 2, 2008.

(51) Int. Cl.
| C12P 19/34 | (2006.01) |
|---|---|
| C12Q 1/68 | (2006.01) |
| G01N 33/00 | (2006.01) |
| C07H 21/02 | (2006.01) |
| C12Q 1/42 | (2006.01) |
| C12N 9/14 | (2006.01) |

(52) U.S. Cl.
CPC .. *C12Q 1/42* (2013.01); *C12N 9/14* (2013.01); *C12P 19/34* (2013.01)

(58) Field of Classification Search
USPC ............ 435/6.1, 6.11, 21, 91.1, 91.51, 91.52; 424/94.5; 536/23.1; 436/94
See application file for complete search history.

(56) References Cited

U.S. PATENT DOCUMENTS

| 5,096,815 A | 3/1992 | Ladner et al. |
|---|---|---|
| 5,198,346 A | 3/1993 | Ladner et al. |
| 5,223,409 A | 6/1993 | Ladner et al. |
| 5,270,163 A | 12/1993 | Gold et al. |
| 5,567,588 A | 10/1996 | Gold et al. |
| 5,580,737 A | 12/1996 | Polisky et al. |
| 5,587,468 A | 12/1996 | Allen et al. |
| 5,597,713 A | 1/1997 | Kato et al. |
| 5,683,867 A | 11/1997 | Biesecker et al. |
| 5,696,249 A | 12/1997 | Gold et al. |
| 5,723,594 A | 3/1998 | Janjic et al. |
| 5,733,731 A | 3/1998 | Schatz et al. |
| 5,773,598 A | 6/1998 | Burke et al. |
| 5,811,238 A | 9/1998 | Stemmer et al. |
| 5,817,785 A | 10/1998 | Gold et al. |
| 5,830,721 A | 11/1998 | Stemmer et al. |
| 5,837,458 A | 11/1998 | Minshull et al. |
| 5,849,546 A | 12/1998 | Sousa et al. |
| 5,861,254 A | 1/1999 | Schneider et al. |
| 5,958,691 A | 9/1999 | Pieken et al. |
| 5,998,142 A | 12/1999 | Gold et al. |
| 6,001,577 A | 12/1999 | Gold et al. |
| 6,013,443 A | 1/2000 | Heilig et al. |
| 6,030,776 A | 2/2000 | Eaton et al. |
| 6,207,446 B1 | 3/2001 | Szostak et al. |
| 7,303,901 B2 | 12/2007 | Hjorleifsdottir et al. |
| 7,452,705 B2 | 11/2008 | Kazmierczak et al. |
| 8,163,491 B2 * | 4/2012 | Jendrisak et al. ............ 435/6.12 |
| 2002/0018774 A1 | 2/2002 | Green et al. |
| 2004/0171041 A1 | 9/2004 | Dahl et al. |

FOREIGN PATENT DOCUMENTS

| EP | 0206200 | 9/1992 |
|---|---|---|
| WO | 0104286 | 1/2001 |
| WO | 0175067 | 10/2001 |

OTHER PUBLICATIONS

Rasmussen et al., In vivo transcriptional pausing and cap formation on three Drosophila heat shock genes. Proc. Natl. Acad. Sci. USA, 90, 7923-7927, 1993.*
Sutton et al., The cap of both miniexon-derived RNA and mRNA of trypanosomes is 7-methylguanosine. Molecular and Cellular Biology, 8, 494-496, 1988.*
"Primase" from Wikipedia, the free encyclopedia. Printed on Jul. 29, 2013.*
Alexander et al., 99th Abs Gen Meeting Am Soc Microbiol, 1999, p. 360, H-164.
Alexander, "Characterization of genetically-programmed responses of *Escherichia coli* to heavy metal stress," Ph. D. Thesis, McGill University, Aug. 2001, retrieved Aug. 22, 2012.
Banerjee, "5'-terminal cap structure in eucaryotic messenger ribonucleic acids," Microbiol. Rev., 44: 175-205, 1980.

(Continued)

*Primary Examiner* — Frank Lu

(57) ABSTRACT

The present invention relates to the discovery of RNA 5' polyphosphatase enzymes not previously described in the art, methods for discovery of said enzymes, compositions of said enzymes, methods for making said enzymes, and various methods and kits for using said enzymes for biomedical research, for human and non-human diagnostics, for production of therapeutic products, and for other applications. In particular, some embodiments provide compositions, kits and methods for employing RNA polyphosphatases for isolation, purification, production, and assay of capped RNA using a biological sample or a sample from an in vitro capping reaction wherein the sample also contains RNA that is not capped. Other embodiments provide compositions, kits and methods wherein RNA polyphosphatases comprise signal-amplifying enzymes for analyte-specific assays.

9 Claims, 2 Drawing Sheets

(56) References Cited

OTHER PUBLICATIONS

Butler and Chamberlin, "Bacteriophage SP6-specific RNA Polymerase," J Biol Chem., 257(10):5772-5778, 1982.
Crameri et al., "Improved green fluorescent protein by molecular evolution using DNA shuffling," Nat. Biotech., 1996, 14:315-319.
Crameri et al., "Molecular evolution of an arsenate detoxification pathway by DNA shuffling," Nat. Biotech., 1997, 15:436-38.
Cwirla et al., "Peptides on phage: A vast library of peptides for identifying ligands," PNAS, 87:6378-x6382, 1990.
Deana et al., "The bacterial enzyme RppH triggers messenger RNA degradation by 5' pyrophosphate removal," Nature, 451: 355-358, 2008.
Deshpande., "Human PIR1 of the protein-tyrosine phosphatase superfamily has RNA 5'-triphosphatase and diphosphatase activities," J. Biol. Chem., 274: 16590-16594, 1999.
Devlin et al., "Random peptide libraries: a source of specific protein binding molecules," Science, 1990, 249:404.
Drummond et al., "The effect of capping and polyadenylation on the stability, movement and translation of synthetic messenger RNAs in *Xenopus* oocytes," Nucleic Acids Res., 13: 7375, 1985.
Dunckley and Parker, "The DCP2 protein is required for mRNA decapping in *Saccharomyces cerevisiae* and contains a functional MutT motif," EMBO J, 18: 5411-5422, 1999.
Dunn et al., "Different template specificities of phage T3 and T7 RNA polymerases," Nature New Biology, 1971, 230:94-96.
Eckert, "DNA Polymerase Fidelity and the Polymerase Chain Reaction," PCR Methods and Applications, 1:17-24, 1991.
Fischer, et al., "Diversity in the signals required for nuclear accumulation of U snRNPs and variety in the pathways of nuclear transport," J. Cell Biol., 113: 705-714, 1991.
Fresco and Buratowski, "Conditional mutants of the yeast mRNA capping enzyme show that the cap enhances, but is not required for, mRNA splicing," RNA, 1996, 2: 584-596.
Fromont-Racine et al.,"A highly sensitive method for mapping the 5' termini of mRNAs," Nucleic Acids Res., 1993, 21:1683-4.
Green et al., "Human beta-globin pre-mRNA synthesized in vitro is accurately spliced in *Xenopus* oocyte nuclei," Cell 32:681-694, 1983.
Gross and Shuman, "Characterization of a baculovirus-encoded RNA 5'-triphosphatase," J. Virology 72: 7057-7063, 1998.
Gunawardana et al., "Identification of functional domains in *Arabidopsis thaliana* mRNA decapping enzyme (AtDcp2)," Nucleic Acids Res. 36: 203-216, 2008.
Hamm et al., "The trimethylguanosine cap structure of U1 snRNA is a component of a bipartite nuclear targeting signal," Cell 62: 569-577, 1990.
Hausmann, "Bacteriophage T7 Genetics," Curr Topics in Microbiol and Immunol, 1976, 75:77-109.
Hermanson, "Bioconjugate Techniques," Academic Press, Inc., San Diego, CA, 1996. Only TOC provided. Will provide specific pages upon Examiner request.
Higman et al., "The mRNA (guanine-7-)methyltransferase domain of the vaccinia virus mRNA capping enzyme. Expression in *Escherichia coli* and structural and kinetic comparison to the intact capping enzyme," J. Biol. Chem. 269:14974-14981, 1994.
Higman. et al., "The vaccinia virus mRNA (guanine-N7-)-methyltransferase requires both subunits of the mRNA capping enzyme for activity," J. Biol. Chem. 267: 16430, 1992.
Ho and Shuman, "Bacteriophage T4 RNA ligase 2(gp24.1) exemplifies a family of RNA ligases found in all phylogenetic domains," PNAS, 99(20):12709-12714, 2002.
Ike et al., "Solid phase synthesis of polynucleotides. VIII. Synthesis of mixed oligodeoxyribonucleotides by the phosphotriester solid phase method," Nucleic Acid Res., 11(2):477-488, 1983.
Itakura et al., "Expression in *Escherichia coli* of a chemically synthesized gene for the hormone somatostatin," Science, 1977, 198:1056-1063.
Itakura et al., Recombinant DNA, in Walton ed., Proceedings of the 3rd Cleveland Symposium on Macromolecules, Elsevier, Amsterdam, 1981, 273-289.
Itakura et al., "Synthesis and use of synthetic oligonucleotides," Annu Rev biochem, 1984, 53:323.
Jedrzejas et al., Structure and mechanism of action of a novel phosphoglycerate mutase from *Bacillus stearothermophilus*, EMBO, 2000, 19(7):1419-1431.
Kazmierczak et al., "The phage N4 virion RNA polymerase catalytic domain in related to single-subunit RNA polymerases," EMBO J, 21(21):5815-5823, 2002.
Keppetipola et al., ""Novel Triphosphate Phosphohydrolase Activity of *Clostridium thermocellum* TTM, a Member of the Triphosphate Tunnel Metalloenzyme Superfamily,"" J Biol Chem, 282(16):11941-11949, 2007.
Korsten et al., "The Strategy of Infection as a Criterion for Phylogenetic Relationships of Non-Coli Phages Morphologically Similar to Phage T7," J Gen Virol, 43:57-73, 1979.
Krieg and Melton, "Functional messenger RNAs are produced by SP6 in vitro transcription of cloned cDNAs," Nucleic Acids Res. 12: 7057, 1984.
Martin et al., "Purification of mRNA guanylyltransferase and mRNA (guanine-7-) methyltransferase from vaccinia virions," J. Biol. Chem. 250: 9322, 1975.
Maruyama et al., "Construction and characterization of a full length-enriched and a 5'-end-enriched cDNA library," Gene 138: 171-174, 1994.
Mattaj, "Cap trimethylation of U snRNA is cytoplasmic and dependent on U snRNP protein binding," Cell 46: 905-911, 1986.
Moore and Arnold, "Directed evolution of a para-nitrobenzyl esterase for aqueous-organic solvents," Nat. Biotech., 1996, 14:458-467.
Myette and Niles, "Domain Structure of the Vaccinia Virus mRNA Capping Enzyme," J. Biol. Chem. 271: 11936-11944, 1996.
Narang, "DNA Synthesis," Tetrahedron Lett, 1983, 39:3-22.
Padilla and Sousa, "A Y639F/H784A T7 RNA polymerase double mutant displays superior properties for synthesizing RNAs with non-canonical NTPs," Nucleic Acids Res., 2002, 15:e138.
Peyrane et al., "High-yield production of short GpppA- and 7MeGp-ppA-capped RNAs and HPLC-monitoring of methyltransfer reactions at the guanine-N7 and adenosine-2'O positions," Nucleic Acid Res., 2007, 35(4)1-11.
Rinn et al., "Functional demarcation of active and silent chromatin domains in human HOX loci by noncoding RNAs," Cell 129: 1311-1323, 2007.
Roberts et al., "Directed evolution of a protein: Selection of potent neutrophil elastase inhibitors displayed on M13 fusion phage," PNAS, 89:2429-2433, 1992.
Ross, "Messenger RNA turnover in eukaryotic cells," Mol. Biol. Med. 5: 1-14, 1988.
Savage et al., Biotin Chemistry: A Handbook, Pierce Chemical Company, 1992, only Table of Contents.
Schwer and Shuman, "Conditional inactivation of mRNA capping enzyme affects yeast pre-mRNA splicing in vivo," RNA 2: 574-583, 1996.
Schwer et al., Nucleic Acids Res. 26: 2050-2057, 1998.
Scott and Smith, "Searching for peptide ligands with an epitope library," Science, 1990, 249:386.
Shuman et al., "Accelerated mRNA decay in conditional mutants of yeast mRNA capping enzyme," J. Biol. Chem. 255: 11588, 1980.
Shuman, "Capping enzyme in eukaryotic mRNA synthesis," Prog Nucleic Acid Res Mol Biol 50: 101-129, 1995.
Shuman, "Structure, mechanism, and evolution of the mRNA capping apparatus," Prog. Nucleic Acid Res. Mol. Biol. 66: 1-40, 2001.
Smith, "Applied evolution. The progeny of sexual PCR," Nature, 1994, 370:324-5.
Song et al., Molecular cloning and characterization of a phosphoglycerate mutase gene from *Clonorchis sinensis*, Parsitol Res, 2007, 101-709-714.
Sousa and Mukherjee, "T7 RNA polymerase," Prog Nucleic Acid Res Mol Biol., 2003, 73:1-41.
Steiger et al., "Analysis of recombinant yeast decapping enzyme," RNA 9: 231-238, 2003.
Stemmer, "DNA shuffling by random fragmentation and reassembly: In vitro recombination for molecular evolution," PNAS, 91:10747-10751, 1994.

(56) References Cited

OTHER PUBLICATIONS

Stemmer, "Rapid evolution of a protein in vitro by DNA shuffling," Nature, 1994, 370:389-391.

Stevens and Poole, "5'Exonuclease-2 of *Saccharomyces cerevisiae*," J Biol Chem, 270(27):16063-16069, 1995.

Suzuki et al., "Construction and characterization of a full length-enriched and a 5'-end-enriched cDNA library," Gene 200: 149-156, 1997.

Suzuki and Sugano, "Construction of full-length-enriched cDNA libraries. The oligo-capping method," Methods in Molecular Biology, 175: 143-153, 2001.

Takagi et al., "A protein tyrosine phosphatase-like protein from baculovirus has RNA 5'-triphosphatase and diphosphatase activities," Proc. Natl. Acad. Sci. USA 95: 9808-9812, 1998.

Towle et al., "Purification and Characterization of Bacteriophage gh-1-induced Deoxyribonucleic Acid-dependent Ribonucleic Acid Polymerase from *Pseudomonas putida*," J Biol Chem, 250(5):1723-1733, 1975.

Van Dijk et al., "Human Dcp2: a catalytically active mRNA decapping enzyme located in specific cytoplasmic structures," EMBO J. 21: 6915-6924, 2002.

Van Gelder et al., "Amplified RNA synthesized from limited quantities of heterogeneous cDNA," PNAS, 87:1663-1667, 1990.

Vasiljeva et al., "Identification of a novel function of the alphavirus capping apparatus. RNA 5'-triphosphatase activity of Nsp2," J Biol Chem, 2000, 275(23):17281-17287.

Wang et al., "Phylogeny of mRNA capping enzymes," Proc. Natl. Acad. Sci. USA 94: 9573, 1997.

Xu et al., "The 26 Nudix hydrolases of *Bacillus cereus*, a close relative of *Bacillus anthracis*," J. Biol. Chem. 279: 24861-24865, 2004.

Zalucki et al., "Selection for efficient translation initiation biases codon usage at second amino acid position in secretory proteins," (Nucleic Acids Res. 35: 5748-5754, 2007.

Zhang et al., "Directed evolution of a fucdosidase from a galactosidase by DNA shuffling and screening," PNAS, 94:4504-4509, 1997.

Zhao and Arnold, "Optimization of DNA shuffling for high fidelity recombination," Nucleic Acid Res., 25(6):1307-1308, 1997.

GenBank Accession No. CAA58754, retrieved Aug. 22, 2012, 1 page.

GenBank Accession No. CP000800, retrieved Aug. 22, 2012, 41 pages.

GenBank Accession No. NP_416755, retrieved Aug. 22, 2012, 3 pages.

GenBank Accession No. X83874, retrieved Aug. 22, 2012, 2 pages.

Hoagland, "Handbook of Fluorescent Probes and Research Products," Ninth Edition, Molecular Probes, Inc., 2002, Only TOC provided, will provide specific passages upon Examiner request, TOC (Table of Content).

Bensing et al., "Sensitive detection of bacterial transcription initiation sites and differentiation from RNA processing sites in the pheromone-induced plasmid transfer system of *Enterococcus faecalis*," PNAS, 1996, 93:7794-7799.

* cited by examiner

FIGURE 1

Examples of Reactions Catalyzed by RNA 5' Polyphosphatase pppN…. or ppN…. $\xrightarrow{\text{RNA 5' polyphosphatase}}$ pN….. + 2Pi $7^{me}$GpppN…. $\xrightarrow{\text{RNA 5' polyphosphatase}}$ No Reaction N = RNA, DNA, NTPs, NDPs, dNTPs, dNDPs

FIGURE 2
DNA and Amino Acid Sequences of *E. coli* RNA 5' Polyphatase

SEQ ID NO: 1: DNA Sequence of *E. coli* RNA 5' Polyphosphatase
The DNA sequence for the first 4 amino acids of amino terminus of the ~24-kD
protein and the ~19-kD protein are in italics or underlined, respectively.

*ATGTTAGCTTTT*TGCCGCTCTTCGTTGAAGTCAAAAAAATATATCATCATT
TTACTGGCGCTCGCTGCAATTGCCGGACTGGGTACTCATGCCGCCTGGA
GT<ins>AGCAATGGTTTG</ins>CCACGTATCGACAATAAAACACTGGCCAGACTGGC
ACAGCAGCACCCGGTTGTCGTTTTGTTTCGTCATGCTGAACGTTGCGAC
CGTTCAACCAATCAATGCTTGTCAGATAAAACAGGTATTACGGTTAAAGG
TACCCAGGATGCCCGTGAACTGGGCAACGCTTTTAGTGCTGATATCCCT
GATTTCGATCTTTATTCCAGTAATACCGTCCGGACCATTCAGTCGGCTAC
CTGGTTTTCAGCGGGTAAAAAATTGACGGTAGATAAACGACTTCTTCAGT
GCGGTAATGAGATTTATAGTGCAATTAAGGACTTACAAAGCAAAGCGCC
TGATAAAAATATCGTTATTTTCACCCATAATCATTGCCTGACATATATTG
CTAAAGATAAGCGTGACGCGACATTTAAACCTGATTATCTGGATGGTTTA
GTCATGCATGTGGAAAAAGGCAAAGTTTATCTGGATGGGGAATTCGTTA
ACCACTAA SEQ ID NO: 2: Translated Amino Acid Sequence of *E. coli* RNA 5' Polyphosphatase
The first 4 amino acids of the amino terminus of the ~24-kD protein and
the ~19-kD protein are in italics or underlined, respectively.

*MLAF*CRSSLKSKKYIIILLALAAIAGLGTHAAWS<ins>SNGL</ins>PRIDNKTLARLAQQH
PVVVLFRHAERCDRSTNQCLSDKTGITVKGTQDARELGNAFSADIPDFDLYS
SNTVRTIQSATWFSAGKKLTVDKRLLQCGNEIYSAIKDLQSKAPDKNIVIFTH
NHCLTYIAKDKRDATFKPDYLDGLVMHVEKGKVYLDGEFVNH

US 9,017,970 B2

RNA POLYPHOSPHATASE COMPOSITIONS, KITS, AND USES THEREOF

The present application claims priority to U.S. application Ser. No. 61/050,041 filed May 2, 2008, which is herein incorporated by reference in its entirety.

FIELD OF THE INVENTION

The present invention relates to the discovery of RNA 5' polyphosphatase enzymes not previously described in the art, methods for discovery of said enzymes, compositions of said enzymes, methods for making said enzymes, and various methods and kits for using said enzymes for biomedical research, for human and non-human diagnostics, for production of therapeutic products, and for other applications. In particular, some embodiments provide compositions, kits and methods for employing RNA polyphosphatases for isolation, purification, production, and assay of capped RNA using a biological sample or a sample from an in vitro capping reaction wherein the sample also contains RNA that is not capped. Other embodiments provide compositions, kits and methods wherein RNA polyphosphatases comprise signal-amplifying enzymes for analyte-specific assays.

BACKGROUND OF THE INVENTION

The chemical moiety on the 5' end of an RNA molecule influences its structure, stability, biochemical processing, transport, biological function and fate in a cell or organism. The chemical moieties commonly found at the 5' end of RNA include triphosphates, monophosphates, hydroxyls, and cap nucleotides. The particular chemical moiety on the 5' end provides important clues to the origin, processing, maturation and stability of the RNA. Characterization of this moiety in a newly identified RNA could even suggest a role for the RNA in the cell.

For example, bacterial mRNAs, small prokaryotic and eukaryotic ribosomal RNAs (e.g., 5S or 5.8S rRNAs), and transfer RNAs (tRNAs) typically have a 5' triphosphate group.

Large ribosomal RNAs (e.g., 18S and 26S or 28S eukaryotic rRNA, or 16S and 23S prokaryotic rRNA), and eukaryotic or viral-encoded micro RNAs (miRNAs) typically have a 5' monophosphate group. At least some initially-generated intron RNA molecules from pre-mRNA splicing reactions also have a 5' phosphate group.

RNase A-degraded RNAs and some other endonucleolytically processed RNA molecules have a 5' hydroxyl group.

Most eukaryotic cellular mRNAs and most eukaryotic viral mRNAs have a "cap" or "cap nucleotide" on their 5' end (e.g., an "$N^7$-methylguanosine" or "$m^7G$" cap nucleoside that is joined via its 5'-carbon to a triphosphate group that, in turn, is joined to the 5'-carbon of the most 5'-nucleotide of the primary mRNA). Still further, some eukaryotic RNAs that are not translated into protein, referred to as "non-coding RNAs" or "ncRNAs," have been described, and some of these are capped. Some capped ncRNAs also have a 3' poly(A) tail, like most eukaryotic mRNAs. For example, Rinn, J L et al. (Cell 129: 1311-1323, 2007) described one capped and polyadenylated 2.2-kilobase ncRNA encoded in the HOXC region of human chromosome 12, termed "HOTAIR," that has profound effects on expression of HOXD genes on chromosome 2. In addition, some other eukaryotic RNAs in a sample, such as small nuclear RNAs ("snRNAs"), and pre-miRNAs, can be capped.

The 5' caps of eukaryotic cellular and viral mRNAs (and some other forms of RNA) play important roles in mRNA metabolism, and are required to varying degrees for processing and maturation of an mRNA transcript in the nucleus, transport of mRNA from the nucleus to the cytoplasm, mRNA stability, and efficient translation of the mRNA to protein. For example, the cap plays a pivotal role in the initiation of protein synthesis and in eukaryotic mRNA processing and stability in vivo. The cap provides resistance to 5' exoribonuclease (XRN) activity and its absence results in rapid degradation of the mRNA (e.g., see Mol. Biol. Med. 5: 1-14, 1988; Cell 32: 681-694, 1983). Thus, mRNA prepared (e.g., in vitro) for introduction (e.g., via microinjection into oocytes or transfection into cells) and expression in eukaryotic cells should be capped.

Many eukaryotic viral RNAs are infectious only when capped, and when RNA molecules that are not capped (i.e., they are "uncapped") are introduced into cells via transfection or microinjection, they are rapidly degraded by cellular RNases (e.g., see Krieg, and Melton, Nucleic Acids Res. 12: 7057, 1984; Drummond, et al. Nucleic Acids Res. 13: 7375, 1979).

The primary transcripts of many eukaryotic cellular genes and eukaryotic viral genes require processing to remove intervening sequences (introns) within the coding regions of these transcripts, and the benefits of the cap also extend to stabilization of such pre-mRNA. For example, it was shown that the presence of a cap on pre-mRNA enhanced in vivo splicing of pre-mRNA in yeast, but was not required for splicing, either in vivo or using in vitro yeast splicing systems (Fresco, L D and Buratowski, S, RNA 2: 584-596, 1996; Schwer, B et al., Nucleic Acids Res. 26: 2050-2057, 1998; Schwer, B and Shuman, S, RNA 2: 574-583, 1996). The enhancement of splicing was primarily due to the increased stability of the pre-mRNA since, in the absence of a cap, the pre-mRNA was rapidly degraded by 5' exoribonuclease (Schwer, B, Nucleic Acids Res. 26: 2050-2057, 1998). Thus, it is also beneficial that transcripts synthesized for in vitro RNA splicing experiments are capped.

While capped mRNA remains in the cytoplasm after being exported from the nucleus, some other RNAs, such as some snRNAs have caps that are further methylated and then imported back into the nucleus, where they are involved in splicing of introns from pre-mRNA to generate mRNA exons (Mattaj, Cell 46: 905-911, 1986; Hamm et al., Cell 62: 569-577, 1990; Fischer, et al., J. Cell Biol. 113: 705-714, 1991). The splicing reaction generates spiced intron RNA that initially comprises RNA that has a 5' monophosphate group.

Enzymes that modify the 5' ends of RNA are useful tools for characterizing, studying, and manipulating various RNA molecules in vitro. For example, alkaline phosphatase (AP) (e.g., APEX™ alkaline phosphatase, EPICENTRE Technologies, Madison, Wis., USA; shrimp alkaline phosphatase, USB, Cleveland, Ohio; or Arctic alkaline phosphatase, New England Biolabs, MA) converts 5' triphosphate groups (e.g., of uncapped primary RNA) and 5' monophosphate groups (e.g., of rRNA) to 5' hydroxyl groups, generating RNAs that have a 5' hydroxyl group, but does not affect capped RNA. Nucleic acid pyrophosphatase (PPase) (e.g., tobacco acid pyrophosphatase (TAP)) cleaves triphosphate groups (e.g., of both capped and uncapped 5'-triphosphorylated RNAs) to synthesize RNAs that have a 5' monophosphate group. A Dcp1/Dcp2 complex decapping enzyme (i.e., a "Dcp2-type" decapping enzyme) (e.g., yeast decapping enzyme, mammalian decapping enzyme, *Arabidopsis thaliana* decapping enzyme, vaccinia virus decapping enzyme, e.g., vaccinia virus decapping enzymes D9 or D10) converts capped RNA (e.g., m7G-capped RNA) to RNA that has a 5' monophosphate group, but does not convert RNA that has a 5' triphosphate group to RNA that has a 5' monophosphate group. A capping enzyme (e.g., poxvirus capping enzyme, vaccinia virus capping enzyme, Saccharomyces cerevisiae capping enzyme, or SCRIPTCAP™ capping enzyme, EPICENTRE) converts RNA that has a 5' triphosphate group or RNA that has a 5' diphosphate group to capped RNA. Polynucleotide kinase (PNK) (e.g., T4 PNK) monophosphorylates hydroxyl groups on the 5' ends of RNA molecules and removes monophosphate groups on the 3' ends of RNA molecules (e.g., 3' monophosphate groups generated from the action of RNase A). Further, 5' exoribonuclease (XRN) (e.g., Saccharomyces cerevisiae Xrn I exoribonuclease, or TERMINATOR™ 5'-phosphate-dependent exonuclease, EPICENTRE) digests 5'-monophosphorylated RNA to mononucleotides, but generally does not digest RNA that has a 5' triphosphate, 5' cap, or 5' hydroxyl group.

The reaction specificity of RNA ligase can also be a useful tool to discriminate between RNA molecules that have different 5' end groups. This enzyme catalyzes phosphodiester bond formation specifically between a 5' monophosphate group in a donor RNA and a 3'-hydroxyl group in an acceptor oligonucleotide (e.g., an RNA acceptor oligonucleotide). Thus, RNAs that have a monophosphate group on their 5' ends, whether present in a sample or obtained by treatment (e.g., by treatment of 5'-triphosphorylated or 5'-capped RNA with TAP) are donor substrates for ligation to an acceptor nucleic acid that has a 3' hydroxyl group using RNA ligase (e.g., T4 RNA ligase, EPICENTRE, or bacteriophage TS2126 RNA ligase, EPICENTRE). RNA molecules that have a 5' triphosphate, diphosphate, hydroxyl or cap nucleotide do not function as donor molecules for RNA ligase. Thus, RNAs that have a hydroxyl group on their 5' ends, whether present in a sample or obtained by treatment (e.g., treatment with AP) cannot serve as donor substrates for RNA ligase. Similarly, RNA molecules that contain a 3'-terminal blocking group (e.g., a 3'-phosphate group or a 3'-beta-methoxyphenylphosphate group) do not function as acceptor substrates for RNA ligase.

Numerous publications disclose use of alkaline phosphatase (AP), tobacco acid pyrophosphatase (TAP), and T4 RNA ligase to manipulate m7G-capped eukaryotic mRNAs (e.g., World Patent Applications WO0104286; and WO 2007/117039 A1; U.S. Pat. No. 5,597,713; Suzuki, Y et al., Gene 200: 149-156, 1997; Suzuki, Y and Sugano, S, Methods in Molecular Biology, 175: 143-153, 2001, ed. by Starkey, MP and Elaswarapu, R, Humana Press, Totowa, N.J.; Fromont-Racine, M et al., Nucleic Acids Res. 21: 1683-4, 1993; and in Maruyama, K and Sugano, S, Gene 138: 171-174, 1994). In those methods, total eukaryotic RNA or isolated polyadenylated RNA is first treated with AP, which converts RNA that has a 5' triphosphate (e.g., uncapped primary RNA) and RNA that has a 5' monophosphate to RNA that has a 5' hydroxyl. Then, the sample is treated with TAP, which converts the 5'-capped eukaryotic mRNA to mRNA that has a 5' monophosphate. The resulting 5'-monophosphorylated mRNA is then ligated to an acceptor oligonucleotide using T4 RNA ligase. The resulting "oligo-capped" mRNA is used for synthesis of first-strand cDNA, and double-stranded cDNA (e.g., to generate a full-length cDNA library and for identification of the 5' ends of eukaryotic mRNA by sequencing or methods such as 5' RACE).

In view of the importance of capped RNAs in gene expression and biological metabolism, there is currently great interest in studying and using the various types of capped RNAs for research, industrial, agricultural and medical purposes.

Thus, what is needed in the art are improved methods for isolation, purification, production, and assay of capped RNA molecules in samples that also contain other uncapped RNA molecules.

Thus, what is needed are methods that enable selective removal of the uncapped RNAs under conditions wherein the capped RNAs are not removed. Enzymes can be useful tools for this purpose. However, prior to the present invention, no well characterized enzyme had been demonstrated in the art for selectively digesting the 5' triphosphate of primary RNA, such as uncapped eukaryotic primary RNA or bacterial mRNA, to a 5' monophosphate without also digesting capped eukaryotic mRNA. This is regrettable because an enzyme with this selective enzymatic activity could be used for isolating, purifying, manufacturing, or quantifying capped RNAs in a sample that also contains uncapped primary RNAs. Thus, what is needed in the art is a well-characterized RNA 5' polyphosphatase enzyme, kits that contain said enzyme, and methods therefor.

What is needed in the art are RNA 5' polyphosphatase compositions that are capable of converting a 5' triphosphate group of a primary RNA transcript to a 5' monophosphate group, and methods for using said RNA polyphosphatase enzyme compositions in order to selectively convert undesired uncapped primary RNAs that have a 5' triphosphate group to RNAs that have a 5' monophosphate group without also converting desired capped RNAs to RNAs that have a 5' monophosphate group.

What is further needed are methods, compositions, and kits that employ one or more other enzymes, in combination with and in addition to an RNA 5' polyphosphatase enzyme composition, in order to selectively remove both RNAs that have a 5' monophosphate group in a sample, as well as the RNAs that have a 5' monophosphate group generated as a product of the RNA 5' polyphosphatase enzymatic reaction, thereby removing those RNAs from the capped RNAs present in the sample (e.g., for preparation of compositions that consist of only capped RNA molecules, e.g., for expression in eukaryotic cells, e.g., in oocytes or somatic cells, e.g., for research and therapeutic applications).

Still further, enzymes that are capable of removing phosphate groups (e.g., phosphatases and pyrophosphatases) are widely known in the art and have been widely used as signal-amplifying substances for detection of biomolecules for research, molecular diagnostics, immunodiagnostics, and other applications. For example, such phosphate-removing enzymes have been widely used for making conjugates with small molecules like biotin or digoxigenin and with nucleic acids or proteins (e.g., streptavidin, protein A, or primary or secondary antibodies) for use as signal-amplifying substances for sensitive detection of nucleic acids, proteins, and other analytes. One widely used phosphate-removing enzyme is alkaline phosphatase derived from calf intestine or bacteria. However, since the signal-amplifying enzymes used in the art are active as homodimers and require divalent metal cations for catalysis, these enzymes may be undesirable for certain assays because their subunits could dissociate, resulting in low assay sensitivity. Also, because the signal-amplifying enzymes in the art require divalent metal cations, their use in some assays is difficult or impossible, or necessitates additional assay steps, which is inconvenient. Thus, what is needed in the art are single-subunit enzymes with phosphate-removing enzymatic activities that are active in the absence of divalent metal ions for use as signal-amplifying substances for sensitive detection of nucleic acids, proteins, or other analytes. What is needed are such single-subunit enzymes that can be used to make conjugates with affinity binding molecules for use as signal-amplifying substances.

Also, since the signal-amplifying enzymes used in the art are active as homodimers, it is more difficult to genetically engineer and make fusion proteins consisting of the signal-amplifying enzyme and a proteinaceous affinity binding molecule (e.g., streptavidin, a single-chain artificial antibody, or protein A). Thus, what is further needed in the art are single-subunit enzymes that can be used to genetically engineer fusion proteins consisting of the signal-amplifying enzyme and a protein affinity binding molecule for use as signal-amplifying substances.

SUMMARY OF THE INVENTION

In some embodiments, the present invention provides compositions comprising a substantially purified RNA polyphosphatase (e.g., from *E. coli*), or purified nucleic acid sequence encoding the RNA polyphosphatase. In some embodiments, the present invention provides compositions comprising a substantially purified RNA polyphosphatase comprising at least six consecutive amino acids of SEQ ID NO: 2.

In certain embodiments, the RNA polyphosphatase comprises at least ten consecutive amino acids of SEQ ID NO: 2 (e.g., at least 10 . . . 15 . . . 20 . . . 25 . . . 30 . . . 50 . . . 70). In other embodiments, the RNA polyphosphatase is at least 70% identical to SEQ ID NO: 2 (e.g., at least 70% . . . 80 . . . 90 . . . or 99%). In some embodiments, the RNA polyphosphatase is at least 80% identical to SEQ ID NO: 2. In further embodiments, the RNA polyphosphatase is at least 90% identical to SEQ ID NO: 2. In some embodiments, the RNA polyphosphatase comprises SEQ ID NO: 2. In other embodiments, the RNA polyphosphatase consists of, or consists essentially of, SEQ ID NO: 2. IN further embodiments, the RNA polyphosphatase consists of SEQ ID NO: 2 with one or more conserved amino acid changes.

In some embodiments, the present invention provides compositions comprising a substantially purified RNA polyphosphatase encoded by a nucleic acid molecule comprising at least eighteen consecutive bases of SEQ ID NO: 1, or a nucleic acid sequence comprising or consisting of SEQ ID NO:1. In particular embodiments, the nucleic acid molecule comprises at least fifty consecutive bases of SEQ ID NO: 1.

In further embodiments, the nucleic acid molecule is substantially homologous to SEQ ID NO: 1. In other embodiments, the nucleic acid molecule is at least 70% homologous to SEQ ID NO: 1 (e.g., at least 70% . . . 80% . . . 90 . . . 99%). In some embodiments, the composition is obtained from a source selected from among: a native source consisting of a bacterial cell, and a recombinant source wherein the gene for the RNA polyphosphatase is expressed in a prokaryotic or eukaryotic host cell. In further embodiments, the native source is an *E. coli* or *Shigella* bacterial cell. In particular embodiments, the RNA polyphosphatase from the *E. coli* or *Shigella* bacterial cell is produced by a method comprising inducing by addition of zinc sulfate to a culture medium in which the bacterial cell is cultured. In other embodiments, the zinc sulfate is 0.2 mM.

In certain embodiments, the present invention provides compositions comprising a substantially purified RNA polyphosphatase, the polyphosphatase encoded by a nucleic acid sequence, wherein the sequence: (a) contains a motif for the phosphoglycerate mutase-like superfamily; (b) is an aluminum-inducible (ais) gene; (c) maps to 50.4 minutes on *E. coli* strain K12 (MG1655), wherein the protein has locus tag b2252; (d) encodes an mRNA that is expressed in a host cell that is complementary to SEQ ID NO: 1; (e) is expressed from a gene for the RNA polyphosphatase that is cloned in a vector in the host cell; (f) is cloned into a vector downstream of a promoter for a T7-type RNA polymerase, wherein the host cell is capable of inducible expression of the T7-type RNA polymerase; (g) is cloned into a vector downstream of a promoter for a T7 RNA polymerase, wherein the host cell is capable of inducible expression of T7 RNA polymerase; (h) is cloned into a a pET vector, wherein the host cell is an *E. coli* cell that is capable of inducible expression of T7 RNA polymerase; (i) is inserted into the chromosome or into an extra-chromosomal DNA of an *E. coli* host cell; or (j) is joined to an inducible promoter and inserted into the chromosome of an *Escherichia coli* host cell using an artificial transposon, selected from among an EZ-TN5™ transposon, a HYPERMU™ or artificial Mu transposon, another artificial transposon that does not encode a transposase enzyme; (k) comprises the complete sequence of SEQ ID NO: 1; or (l) comprises nucleotides 103 through 603 of SEQ ID NO: 1.

In other embodiments, the substantially purified RNA polyphosphatase: (a) comprises a single polypeptide that exhibits an amino acid sequence comprising at least six consecutive amino acids of SEQ ID NO: 2; (b) has a molecular weight of approximately 24 kD; (c) exhibits an amino acid sequence wherein the first four amino acids of the amino terminus are MLAF; (d) has a molecular weight of approximately 19 kD; (e) exhibits an amino acid sequence wherein the first four amino acids of the amino terminus are SNGL; (f) is active in the presence of EDTA and its enzymatic activity is inhibited by the presence of $Mg^{2+}$ cations of a concentration of 1 mM or greater in the enzyme reaction mixture; (g) has an enzymatic activity that is at least 50-fold higher when 6,8-difluoro-4-methylumbelliferyl phosphate (DiFMUP) is used as a substrate compared to when 4-methylumbelliferyl phosphate (4-MUP) is used as a substrate wherein the reaction buffer consists of 50 mM HEPES/KOH, pH 7.5, 0.1 M NaCl, 1 mM EDTA, 0.1% BME and 0.01% TRITON X100; or (h) is purified or isolated from the periplasmic fraction of the cell in which it is expressed. In some embodiments, the present invention provides a kit comprising an RNA polyphosphatase.

In certain embodiments, the present invention provides kits comprising an RNA 5' polyphosphatase, in combination with at least one other component selected from the group consisting of: a 5' exoribonuclease; a polynucleotide kinase; an RNA 5' monophosphatase; and a capping enzyme system. In some embodiments, the RNA 5' polyphosphatase is selected from the group consisting of an aluminum-inducible RNA 5' polyphosphatase, *E. coli* RNA 5' polyphosphatase I and *Shigella* RNA 5' polyphosphatase I; the 5' exoribonuclease is selected from the group consisting of *Saccharomyces cerevisae* Xrn I exoribonuclease and TERMINATOR™ 5'-phosphate-dependent exonuclease; the polynucleotide kinase is selected from T4 polynucleotide kinase; and the capping enzyme is selected from the group consisting of a poxvirus capping enzyme system, vaccinia capping enzyme system, *Saccharomyces cerevisiae* capping enzyme system, and the SCRIPTCAP™ capping enzyme kit.

In some embodiments, the present invention provides kits comprising an RNA polyphosphatase and a storage or reaction buffer substantially lacking magnesium.

In other embodiments, the present invention provides kits comprising an RNA polyphosphatase and a reaction buffer comprising one or more of Tris-HCl, NaCl, HEPES-KOH, EDTA, β-mercaptoethanol, TRITON X-100, and RNase free water.

In particular embodiments, the present invention provides kits comprising an RNA polyphosphatase and a storage buffer comprising one or more of glycerol, Tris-HCl, NaCl, EDTA, dithiothretol, and Triton X-100.

In additional embodiments, the present invention provides methods for identifying, obtaining, isolating or purifying an RNA polyphosphatase in a sample containing proteins from cells or an extract or fraction of cells, the method comprising the steps of: (A) separating the proteins in the sample, thereby obtaining a collection of solutions of separated proteins; (B) contacting each of the solutions of separated proteins with an RNA molecule that has a 5' triphosphate or 5' diphosphate group, wherein at least one of the beta or gamma phosphates in the group is labeled, under conditions described herein wherein an RNA polyphosphatase is active, and detecting whether the labeled beta or gamma phosphate is removed from the RNA molecule; and (C) identifying, among those solutions of separated proteins wherein the labeled beta or gamma phosphate of the RNA molecule was removed, those solutions of separated proteins wherein the 5' alpha phosphate on the RNA molecule is present, thereby identifying, obtaining, isolating or purifying the RNA polyphosphatase.

In particular embodiments, step (3) of identifying those solutions of separated proteins wherein the 5' alpha phosphate on the RNA molecule is present comprises the step of: contacting the RNA molecule wherein the labeled phosphate was removed in step (2) with a 5' exoribonuclease under conditions and for sufficient time wherein the 5' exoribonuclease digests RNA that has a 5' monophosphate group but does not digest RNA that has a 5' triphosphate or 5' diphosphate group, wherein digestion of the RNA molecule identifies the presence of an RNA polyphosphatase.

In some embodiments, the step (3) of identifying those solutions of separated proteins wherein the 5' alpha phosphate on the RNA molecule is present comprises the step of: contacting the RNA molecule wherein the labeled phosphate was removed in step (2) with an RNA acceptor oligonucleotide and an RNA ligase under conditions and for sufficient time wherein the RNA acceptor oligonucleotide is ligated to the 5' end of the RNA molecule that has a 5' monophosphate group, wherein ligation of the RNA acceptor oligonucleotide to the RNA molecule identifies the presence of an RNA polyphosphatase.

In other embodiments, the present invention provides methods for converting RNA that has a 5' polyphosphate group to RNA that has a 5' monophosphate group, wherein the method does not convert capped RNA to RNA that has a 5' monophosphate group, the method comprising: (1) providing a sample that contains capped RNA and RNA that has a 5' polyphosphate group; and an RNA polyphosphatase; and (2) contacting the sample with the RNA polyphosphatase under conditions and for sufficient time wherein all phosphates except the 5' alpha monophosphate group are removed and RNA that has a 5' monophosphate is generated.

In additional embodiments, the RNA that has a 5' polyphosphate group is selected from among an RNA that has a 5' triphosphate group and RNA that has a 5' diphosphate group. In some embodiments, the RNA that has a 5' triphosphate group is selected from among: primary eukaryotic RNA; primary prokaryotic RNA; ncRNA; and RNA that is synthesized in an in vitro transcription reaction using an RNA polymerase, including wherein the in vitro transcription reaction is part of an RNA amplification reaction. In further embodiments, the RNA that has a 5' diphosphate group is the product of digestion of a primary RNA transcript with an RNA triphosphatase of a capping enzyme system.

In some embodiments, the present invention provides methods for obtaining, isolating, or purifying capped RNA that is present in a sample that also contains at least one uncapped RNA, the method comprising the steps of: (1) providing: a sample that contains capped RNA and at least one uncapped RNA selected from the group consisting of RNA that has a 5' polyphosphate group and RNA that has a 5' monophosphate group; an RNA polyphosphatase; and a 5' exoribonuclease; (2) contacting the sample from step (1) with the RNA polyphosphatase under conditions and for sufficient time wherein the RNA that has a 5' polyphosphate group is converted to RNA that has a 5' monophosphate group; and (3) contacting the sample from step (2) with the 5' exoribonuclease under conditions and for sufficient time wherein RNA that has a 5' monophosphate group is digested, but capped RNA is not digested, thereby obtaining, isolating, or purifying the capped RNA.

In particular embodiments, the RNA that has a 5' polyphosphate group is selected from the group consisting of RNA that has a 5' triphosphate group and RNA that has a 5' diphosphate group. In further embodiments, the capped RNA that is obtained, isolated, or purified is used for transforming a eukaryotic cell for therapeutic or research applications. In some embodiments, the capped RNA that is obtained, isolated, or purified is used for transfecting antigen-presenting cells (APCs), selected from among dendritic cells, macrophages, epithelial cells, and an artificial APC for preparing a vaccine. In other embodiments, the capped RNA provided in step (1) is obtained from a biological sample or is obtained from an in vitro capping reaction selected from among a co-transcriptional in vitro capping reaction comprising an RNA polymerase and a dinucleotide cap analog and a post-transcriptional in vitro capping reaction comprising a capping enzyme system. In additional embodiments, the capped RNA comprises bacterial mRNA that is capped in vitro using a capping enzyme system.

In certain embodiments, the method additionally comprises quantifying the amount of the capped RNA in the sample, the method further comprising the substeps of: (1)(a) quantifying the amount of total RNA in the sample; and (4) quantifying the amount of RNA that was not digested in step (3), thereby quantifying the amount of capped RNA in the sample. In other embodiments, the method further comprises quantifying the amount of RNA that was digested in step (3), thereby quantifying the amount of uncapped RNA in the sample. In certain embodiments, step (4) comprises quantifying the capped RNA by: (measuring fluorescence of RIBOGREEN DYE bound to the RNA; or by precipitating the RNA with 2.5 M ammonium acetate or 0.3 M sodium or potassium acetate and ethanol or isopropanol, resuspending the pellets in water, and quantifying the RNA spectrophotometrically based on the $A_{260}$ extinction coefficient. In further embodiments, the sample provided in step (1) additionally comprises RNA that has a 5' monophosphate group and the method further comprises quantifying the amount of RNA that has a 5' monophosphate group in the sample, wherein, prior to step (2) of contacting the sample with the RNA polyphosphatase, the method additionally comprises the substeps of: (1)(b) contacting the sample provided in step (1) with the 5' exoribonuclease under conditions and for sufficient time wherein RNA in the sample that has a 5' monophosphate group is digested but capped RNA and RNA that has a 5' polyphosphate group is not digested; and (1)(c) quantifying the amount of RNA that was digested or the amount of RNA that was not digested in step (1)(b), whereby the amount of RNA in the sample that was digested indicates the amount of RNA in the sample that has a 5' monophosphate group.

In some embodiments, the sample provided in step (1) comprises RNA that has a 5' monophosphate group, wherein prior to step (2) of contacting the sample with the RNA polyphosphatase, the method additionally comprises the substeps of: additionally providing an RNA 5' monophosphatase in step (1), and contacting the sample provided in step (1) with the RNA 5' monophosphatase under conditions and for sufficient time wherein RNA in the sample that has a 5' monophosphate group is converted to RNA that has a 5' hydroxyl group, whereby the amount of RNA in the sample that is digested by the 5' exoribonuclease in step (3) indicates the amount of RNA in the sample that has a 5' polyphosphate, but does not indicate the amount of RNA in the sample that has a 5' monophosphate group.

In further embodiments, the RNA 5' monophosphatase is inactivated or removed prior to step (2), or wherein the RNA 5' monophosphatase is inactivated by the reaction conditions employed in step (2). In other embodiments, the sample provided in step (1) additionally comprises RNA that has a 5' hydroxyl group, wherein the method additionally comprises providing a polynucleotide kinase and ATP in step (1), and the method further comprises the steps of: (5) contacting the sample from step (3) with polynucleotide kinase and the ATP under conditions and for sufficient time wherein RNA that has a 5' hydroxyl group is phosphorylated to RNA that has a 5' monophosphate group; (6) contacting the sample from step (5) with the 5' exoribonuclease under conditions and for sufficient time wherein RNA that has a 5' monophosphate group is digested, but capped RNA and RNA that has a 5' polyphosphate group and RNA that has a 5' hydroxyl group are not digested; and (7) quantifying the amount of RNA that was digested or the amount of RNA that was not digested in step (6), whereby the amount of RNA in the sample that was digested indicates the amount of RNA in the sample that has a 5' hydroxyl group.

In some embodiments, the present invention provides kits for obtaining, isolating or purifying capped RNA that is present in a sample or for quantifying its amount, the kit comprising: (1) an RNA polyphosphatase (RPP) selected from the group consisting of an aluminum-inducible RPP, *E. coli* RPP I, and *Shigella* RPP I; and (2) a 5' exoribonuclease (XRN) selected from the group consisting of TERMINATOR™ 5'-phosphate-dependent exonuclease and *Saccharomyces cerevisae* Xrn I exoribonuclease (Xrn I)).

In particular embodiments, the kit additionally comprises a polynucleotide kinase (PNK). In other embodiments, the kit additionally comprises RNA 5' monophosphatase.

In some embodiments, the present invention provides compositions comprising an RNA polyphosphatase that is conjugated to an affinity binding molecule. In certain embodiments, the affinity binding molecule is selected from the group consisting of: (a) a nucleic acid comprising DNA or RNA; (b) a protein; (c) a glycoprotein; (d) a lipoprotein; (e) a carbohydrate; (f) a lipid; (g) a lectin; (h) a hormone; (i) a hormone receptor; (j) biotin; (k) avidin or streptavidin; (l) protein A; (m) protein G; (n) an antibody; (O) an antigen; and (p) digoxigenin.

In some embodiments, the present invention provides methods for labeling an affinity binding molecule, the method comprising the steps of: (i) providing:RNA polyphosphatase; an affinity binding molecule; and a chemical conjugation reagent; and (ii) contacting the RNA polyphosphatase with the affinity binding molecule and the chemical conjugation reagent under conditions wherein the RNA polyphosphatase is joined to the affinity binding molecule, wherein the enzymatic activity of the RNA polyphosphatase and the ability of the affinity binding molecule to form a specific binding pair are retained.

In further embodiments, the affinity binding molecule is selected from the group consisting of a nucleic acid probe, a protein, streptavidin, biotin, protein A, an antibody, an artificial antibody, an aptamer selected using SELEX, and digoxigenin.

In some embodiments, the present invention provides methods for preparing a signal-amplifying substance consisting of RNA polyphosphatase that is conjugated or bound to an affinity binding molecule, the method comprising the steps of: (a) providing: a reactive affinity binding molecule consisting of an affinity binding molecule with a reactive moiety; and RNA polyphosphatase; and (b) contacting the reactive affinity binding molecule with the RNA polyphosphatase under conditions wherein the reactive affinity binding molecule is covalently joined to the RNA polyphosphatase, wherein the enzymatic activity of the RNA polyphosphatase and the ability of the affinity binding molecule to form a specific binding pair are retained.

In further embodiments, the affinity binding molecule is selected from the group consisting of a nucleic acid probe, a protein, streptavidin, biotin, protein A, an antibody, an artificial antibody, an aptamer selected using SELEX, and digoxigenin.

In some embodiments, the present invention the present invention provides compositions comprising a recombinant fusion protein consisting of an RNA polyphosphatase (RPP), selected from the group consisting of an aluminum-inducible RPP, *E. coli* RPP I, and *Shigella* RPP I, and a protein that is an analyte-binding substance (ABS), selected from the group consisting of streptavidin, a single-chain artificial antibody, and protein A. In certain embodiments, the present invention provides a reaction mixture formed by combining an RNA polyphosphatase with a sample comprising RNA.

In certain embodiments, the present invention provides an expression vector encoding an RNA polyphosphatase, or a host cell containing such a vector.

In some embodiments, the present invention provides a recombination host cell that contains a gene that encodes an RNA polyphosphatase from a recombinant source, wherein the gene was introduced into the host cell in a recombinant vector or in an artificial transposon. In certain embodiments, the recombinant host cell is a bacterial cell that expresses mRNA that is complementary to the sequence exhibited by the gene that encodes the RNA polyphosphatase from the recombinant source. In other embodiments, the mRNA expressed by the recombinant host cell is complementary to SEQ ID NO: 1, or to the sequence comprising nucleotides 103 through 600 of SEQ ID NO: 1. In other embodiments, the recombinant host cell is an *E. coli* host cell.

In certain embodiments, the present invention provides methods of modifying nucleic acid comprising: modifying an RNA molecule by exposing a sample comprising the RNA molecule to an RNA polyphosphatase.

DESCRIPTION OF THE FIGURES

FIG. 1 shows examples of reactions catalyzed by RNA 5' polyphosphatase.

FIG. 2 shows the DNA and amino acid sequences of *E. coli* RNA 5' polyphosphatase.

DESCRIPTION OF THE INVENTION

We have discovered a novel class of enzymes that we call "RNA 5' polyphosphatases" or simply, "RNA polyphosphatases." RNA polyphosphatases convert RNA that has a 5' polyphosphate group, but not capped RNA, to RNA that has a 5' monophosphate group (FIG. 1). We discovered RNA polyphosphatases as a result of our search for a protein that is capable of removing the beta and gamma phosphates from primary RNA transcripts. Surprisingly, unlike enzymes known in the art, RNA polyphosphatases remove the beta and gamma phosphates from primary RNA transcripts, while leaving the alpha phosphate attached to the 5' end of the RNA, and do not digest the triphosphate bridge of capped RNA (e.g., m$^7$G-capped RNA). To our knowledge, no enzyme has been reported with this specificity of enzymatic activities. Following treatment of primary RNA molecules with an RNA polyphosphatase, the RNA molecules are rendered degradable by 5' exoribonuclease (e.g., Xrn I exoribonuclease).

Various methods for use of RNA polyphosphatases are presented below. Based on the description herein, those with knowledge in the art will know and understand other methods for using RNA polyphosphatases, either alone or in combination with other enzymes, all of which methods are within the scope of the present invention.

One embodiment of the present invention is a purified composition of RNA polyphosphatase. In some embodiments, the purified composition of RNA polyphosphatase is substantially purified, such that it is the most prevalent protein present in the composition. In some embodiments, the purified composition is separated from a majority of other cellular components of a cell from which the RNA polyphosphatase is derived.

In some embodiments, the purified composition of RNA polyphosphatase is obtained from a native source. In some embodiments, the native source is a bacterial cell. In some embodiments, the RNA polyphosphatase from a native source comprising a bacterial cell is induced by the presence of aluminum or zinc ions in the culture medium. In some embodiments, the native source is an *E. coli* or *Shigella* bacterial cell. In some embodiments, the RNA polyphosphatase from the *E. coli* or *Shigella* bacterial cell is induced to a level that is at least 10-fold higher by addition of, for example, 0.2 mM zinc sulfate to a culture medium in which the bacterial cell is cultured. In some embodiments, the RNA polyphosphatase is an approximately 19-kD periplasmic protein. In some embodiments, the RNA polyphosphatase is isolated from the periplasmic fraction.

In other embodiments, the purified RNA polyphosphatase composition is obtained from a recombinant source, wherein the gene for the RNA polyphosphatase is expressed in a prokaryotic or eukaryotic host cell. For example, in some embodiments, the purified RNA polyphosphatase composition is obtained from a recombinant source wherein the gene exhibits a sequence that comprises at least 18 consecutive nucleotides of SEQ ID NO: 1 (FIG. 2). In some of these embodiments, the sequence exhibited by the gene contains a motif for the phosphoglycerate mutase-like superfamily. In some of these embodiments, the sequence exhibited by the gene is for an aluminum-inducible (ais) gene. In some of these embodiments, sequence exhibited by the gene maps to 50.4 minutes on *E. coli* strain K12 (MG1655), wherein the protein has locus tag b2252. In some of the embodiments of the invention, the RNA polyphosphatase is obtained from a recombinant source wherein the gene exhibits the complete sequence of SEQ ID NO: 1. In some of the embodiments of the invention, the RNA polyphosphatase is obtained from a recombinant source wherein the gene exhibits a sequence comprising nucleotides 103 through 603 of SEQ ID NO: 1. In some embodiments, the sequence encoding the polyphosphatase in any embodiment of the invention, has greater than 70% (e.g., greater than 80%, greater than 90%, greater than 95%, greater than 98%) sequence identity to SEQ ID NO:1. For example in some embodiments, the sequence encoding the polyphosphatase has 71% or more sequence identity with SEQ ID NO:1 (e.g., 71% . . . 75% . . . 80% . . . 85% . . . 90% . . . 95% . . . or 100% sequence identity with SEQ ID NO:1).

In some of these embodiments, the RNA polyphosphatase composition from the recombinant source is expressed from a sequence exhibited by the RNA polyphosphatase gene that is cloned in a vector in the host cell. In some embodiments, the sequence exhibited by the RNA polyphosphatase gene is cloned into a vector downstream of a promoter for a T7-type RNA polymerase, wherein the host cell is capable of inducible expression of said T7-type RNA polymerase. In some embodiments, the sequence exhibited by the RNA polyphosphatase gene is cloned into a vector downstream of a promoter for a T7 RNA polymerase and the host cell is capable of inducible expression of T7 RNA polymerase. In some embodiments of the invention, including embodiments of any of the methods that employ an RNA polyphosphatase, the sequence exhibited by the RNA polyphosphatase gene is cloned in a pET vector, wherein the host cell is an *E. coli* cell that is capable of inducible expression of T7 RNA polymerase.

In other embodiments, the RNA polyphosphatase from the recombinant source is expressed from a sequence exhibited by the RNA polyphosphatase gene that is inserted into the chromosome or into an extrachromosomal DNA of the host cell. In some of these embodiments, the host cell is an *E. coli* host cell. In some embodiments, the gene for the RNA polyphosphatase is joined to an inducible promoter and inserted into the chromosome of an *Escherichia coli* host cell using an artificial transposon (e.g., an EZ-TN5™ transposon or a HYPERMU™ transposon (EPICENTRE, Madison, Wis.) or another artificial transposon that does not encode a transposase enzyme), wherein the RNA polyphosphatase gene is capable of being expressed. An EZ-TN5 transposon or a HYPERMU™ transposon is an "artificial transposon," by which is meant that it does not encode a transposase gene and, therefore, it is incapable of transposition without providing an exogenous source of the transposase that can use the transposon recognitions sequences within said artificial transposon to effect transposition.

Another embodiment of the invention is a recombinant host cell that contains a gene that encodes an RNA polyphosphatase from a recombinant source, wherein the gene was introduced into the host cell in a recombinant vector or in an artificial transposon. In some embodiments, the recombinant host cell is a bacterial host cell and the recombinant host cell expresses mRNA that is complementary to the sequence exhibited by the gene that encodes an RNA polyphosphatase from a recombinant source. In some embodiments the mRNA expressed by the recombinant host cell is complementary to SEQ ID NO: 1, or to a sequence comprising nucleotides 103 through 600 of SEQ ID NO: 1. In some of these embodiments, the recombinant host cell is an *E. coli* host cell.

In some embodiments, the purified RNA polyphosphatase composition comprises a single polypeptide that exhibits an amino acid sequence comprising at least six consecutive amino acids of SEQ ID NO: 2. In some of these embodiments, the RNA polyphosphatase has a molecular weight of approximately 24 kD. In some of these embodiments, the RNA polyphosphatase exhibits an amino acid sequence wherein the first four amino acids of the amino terminus are MLAF. In some of these embodiments, the RNA polyphosphatase has a molecular weight of approximately 19 kD. In some of these embodiments, RNA polyphosphatase exhibits an amino acid sequence wherein the first four amino acids of the amino terminus are SNGL.

In some embodiments of the invention, the purified RNA polyphosphatase composition is active in the presence of EDTA and its enzymatic activity is inhibited by the presence of $Mg^{2+}$ cations of a concentration of 1 mM or greater in the enzyme reaction mixture. In some embodiments, the purified RNA polyphosphatase has optimal activity in a reaction mixture over a pH range between 5.0 and 8.0. In some embodiments, the RNA polyphosphatase has an enzymatic activity that is at least 50-fold higher when 6,8-difluoro-4-methylumbelliferyl phosphate (DiFMUP) is used as a substrate compared to when 4-methylumbelliferyl phosphate (4-MUP) is used as a substrate wherein the reaction buffer consists of 50 mM HEPES/KOH, pH 7.5, 0.1 M NaCl, 1 mM EDTA, 0.1% BME and 0.01% TRITON X100. In some embodiments, the purified RNA polyphosphatase composition is purified or isolated from the periplasmic fraction of the cell in which it is expressed.

Another embodiment of the invention is a kit comprising RNA 5= polyphosphatase (e.g., an aluminum-inducible RNA 5' polyphosphatase, e.g., *E. coli* RNA 5' polyphosphatase I (*E. coli* RPP I or RPP I, EPICENTRE) or *Shigella* RNA 5' polyphosphatase I), alone, or in combination with at least one other component selected from the group consisting of: a 5' exoribonuclease (XRN) (e.g., *Saccharomyces cerevisae* Xrn I exoribonuclease (Xrn I), or TERMINATOR™ 5'-phosphate-dependent exonuclease, EPICENTRE); a polynucleotide kinase (PNK) (e.g., T4 PNK, EPICENTRE); an RNA 5' monophosphatase (RMP) (e.g., RNA 5' monophosphatase 1 or RMP1, EPICENTRE); and a capping enzyme system (e.g., poxvirus capping enzyme system, vaccinia capping enzyme system, *Saccharomyces cerevisiae* capping enzyme system, or SCRIPTCAP™ capping enzyme kit, EPICENTRE). Kits may comprise a container (e.g., box) housing one or more sub-containers (e.g., tubes or vials) that each contain one or more of the above reagents. Reagents may be provided in solution (e.g., in a suitable storage or reaction buffer solution) or in dried (e.g., lyophilized) form. Kits may further contain control reagents (e.g., RNA molecules), instructions for use, software, or other components useful, necessary, or sufficient for carrying out a desired biological reaction or series of reactions, such as those described herein.

Another embodiment of the present invention is a method for identifying, obtaining, isolating or purifying an RNA polyphosphatase in a sample containing proteins from cells or an extract or fraction of cells, the method comprising the steps of: (A) separating the proteins in the sample (e.g., based on size, charge, or charge density), thereby obtaining a collection of solutions of separated proteins; (B) contacting each of the solutions of separated proteins with an RNA molecule that has a 5' triphosphate or 5' diphosphate group, wherein at least one of the beta or gamma phosphates in said group is labeled, under conditions (e.g., as described herein) wherein an RNA polyphosphatase is active, and detecting whether the labeled beta or gamma phosphate is removed from the RNA molecule; and (C) identifying, among those solutions of separated proteins wherein the labeled beta or gamma phosphate of the RNA molecule was removed, those solutions of separated proteins wherein the 5' alpha phosphate on the RNA molecule is present, thereby identifying, obtaining, isolating or purifying the RNA polyphosphatase.

In some embodiments, step (C) of identifying those solutions of separated proteins wherein the 5' alpha phosphate on the RNA molecule is present comprises the step of contacting the RNA molecule wherein the labeled phosphate was removed in step (B) with a 5' exoribonuclease (XRN) (e.g., *Saccharomyces cerevisae* Xrn I exoribonuclease (Xrn I), or TERMINATOR™ 5'-phosphate-dependent exonuclease, EPICENTRE) under conditions and for sufficient time wherein the 5' exoribonuclease digests RNA that has a 5' monophosphate group but does not digest RNA that has a 5' triphosphate or 5' diphosphate group, wherein digestion of the RNA molecule identifies the presence of an RNA polyphosphatase.

In some embodiments, step (C) of identifying those solutions of separated proteins wherein the 5' alpha phosphate on the RNA molecule is present comprises the step of contacting the RNA molecule wherein the labeled phosphate was removed in step (B) with an RNA acceptor oligonucleotide and an RNA ligase (e.g., T4 RNA ligase, or bacteriophage TS2126 RNA ligase, EPICENTRE) under conditions and for sufficient time wherein the RNA acceptor oligonucleotide is ligated to the 5' end of the RNA molecule that has a 5' monophosphate group, wherein ligation of the RNA acceptor oligonucleotide to the RNA molecule identifies the presence of an RNA polyphosphatase.

Another embodiment of the invention is a method for converting RNA that has a 5' polyphosphate group to RNA that has a 5' monophosphate group, wherein the method does not convert capped RNA to RNA that has a 5' monophosphate group, the method comprising: (1) providing a sample that contains capped RNA and at least one RNA that has a 5' polyphosphate group; and an RNA polyphosphatase (e.g., a purified 5' RNA polyphosphatase); and (2) contacting the sample with the RNA polyphosphatase under conditions and for sufficient time wherein all phosphates except the 5' alpha monophosphate group are removed and RNA that has a 5' monophosphate is generated.

In some embodiments of the method, the RNA that has a 5' polyphosphate group is selected from among a RNA that has a 5' triphosphate group and RNA that has a 5' diphosphate group.

In some embodiments wherein the RNA that has a 5' polyphosphate group comprises or consists of RNA that has a 5' triphosphate group, the RNA that has a 5' triphosphate group is selected from among: primary eukaryotic RNA; primary prokaryotic RNA (e.g., bacterial mRNA); ncRNA; and RNA that is synthesized in an in vitro transcription reaction using an RNA polymerase, including from an in vitro transcription reaction that is part of an RNA amplification reaction.

In some embodiments wherein the RNA that has a 5' polyphosphate group comprises or consists of RNA that has a 5' diphosphate group, the RNA that has a 5' diphosphate group is the product of digestion of a primary RNA transcript with an RNA triphosphatase of a capping enzyme system (e.g., poxvirus capping enzyme, vaccinia capping enzyme, *Saccharomyces cerevisiae* capping enzyme, or SCRIPTCAP™ capping enzyme kit, EPICENTRE).

In some embodiments of the method for converting RNA that has a 5' polyphosphate group to RNA that has a 5' monophosphate group, the method is used for preparing an improved composition of capped RNA molecules wherein the composition contains a higher percentage of capped RNA molecules relative to uncapped RNA molecules (e.g., for study or for use for expression in eukaryotic cells, e.g., in oocytes or somatic cells, for research and therapeutic applications). For example, in some embodiments, the method is used for preparing an improved composition of capped RNA molecules that has a higher percentage of capped RNA molecules relative to uncapped RNA molecules following synthesis of capped RNA molecules using an in vitro capping enzyme system (e.g., selected from among poxvirus capping enzyme, *Saccharomyces cerevisiae* capping enzyme, and SCRIPTCAP™ capping enzyme, including in the mSCRIPT™ mRNA production system, EPICENTRE, Madison, Wis.) or using cap analog (e.g., an ARCA anti-reverse cap analog) in a co-transcriptional capping system (e.g., the MESSAGEMAX™ T7 ARCA-CAPPED MESSAGE TRANSCRIPTION KIT, EPICENTRE, Madison, Wis.). For example, in some embodiments, said method is used for preparing improved compositions of capped RNA molecules for transformation of dendritic cells that are used in making therapeutic vaccines.

Thus, one specific embodiment of the method for converting RNA that has a 5' polyphosphate group to RNA that has a 5' monophosphate group, is used for obtaining, isolating, or purifying capped RNA that is present in a sample that contains at least one uncapped RNA, the method comprising the steps of: (1) providing: a sample that contains capped RNA and at least one uncapped RNA selected from the group consisting of RNA that has a 5' polyphosphate group (e.g., RNA that has a 5' triphosphate group (i.e., primary RNA) or RNA that has a 5' diphosphate group) and optionally, RNA that has a 5' monophosphate group; an RNA polyphosphatase; and, additionally, a 5' exoribonuclease; (2) contacting the sample from step (1) with the RNA polyphosphatase under conditions and for sufficient time wherein the RNA that has a 5' polyphosphate group is converted to RNA that has a 5' monophosphate group; and additionally, (3) contacting the sample from step (2) with the 5' exoribonuclease under conditions and for sufficient time wherein RNA that has a 5' monophosphate group is digested, but capped RNA is not digested, thereby obtaining, isolating, or purifying the capped RNA.

This embodiment of the invention is a method for preparing improved compositions of capped RNA molecules that have a higher percentage of capped RNA molecules relative to uncapped RNA molecules from a mixture that also contains uncapped primary RNA, or RNA that has a 5' diphosphate or, optionally, RNA that has a 5' monophosphate group. This method is useful for removing uncapped RNA from capped RNA (e.g., for transforming cells, e.g., for therapeutic or research applications). For example, in one embodiment of the method, the capped RNA that is obtained, isolated, or purified using this method is used for transfecting antigen-presenting cells (APCs), selected from among dendritic cells, macrophages, epithelial cells, and an artificial APC (e.g., for preparing a vaccine). The APCs (e.g., dendritic cells) express proteins encoded by the capped RNAs and the expressed proteins, in turn, are digested into peptides by enzymes in the APCs, which peptides are presented on the surface of APCs to other immune system cells, thereby inducing an immune response.

In some embodiments, the solution containing the capped RNA and the at least one uncapped RNA that is provided in step (1) is obtained from a biological sample.

In some embodiments, the sample containing the capped RNA and the at least one uncapped RNA that is provided in step (1) is obtained from an in vitro capping reaction selected from among: a co-transcriptional in vitro capping reaction using an RNA polymerase and a dinucleotide cap analog; and a post-transcriptional in vitro capping reaction using a capping enzyme system.

In some other embodiments, the sample containing the capped RNA and the at least one uncapped RNA that is provided in step (1) is obtained from a co-transcriptional in vitro reaction comprising: incubating a DNA template that is functionally joined to an RNA polymerase promoter with an RNA polymerase that recognizes said RNA polymerase promoter, a dinucleotide cap analog and NTPs, under conditions and for sufficient time wherein RNA comprising capped RNA and uncapped RNA is synthesized. In these embodiments, the method can be used to obtain RNA that is greater than 80%, greater than 90%, or greater than 95%, capped, even if only a low percentage of the RNA is capped (e.g., if the ratio of dinucleotide cap analog to GTP in the in vitro transcription reaction is low). Many dinucleotide cap analogs are known in the art. The capped RNA can contain any dinucleotide cap analog that is known in the art provided that it is incorporated by the RNA polymerase used for the in vitro transcription reaction. For example, in some embodiments, the cap analog is selected from the among: GpppG; $m^7$GpppG; $m^7$GpppA; $m_2^{7,3'-O}$GpppG ARCA; $m_2^{7,2'-O}$GpppG; variants of any of the preceding cap analogs that have a tetraphosphate (pppp) internucleoside linkage in place of the triphosphate internucleoside linkage between the cap nucleotide and the other nucleoside of the cap analog; and variants of any of the preceding cap analogs that have a thiophosphate in place of one or more phosphates of the triphosphate or tetraphosphate internucleoside linkage.

In some other embodiments, the sample containing the capped RNA and the at least one uncapped RNA that is provided in step (1) is obtained from a post-transcriptional in vitro capping reaction comprising a capping enzyme system. In these embodiments, the method further comprises incubating uncapped RNA, consisting of RNA that has a 5' triphosphate group or RNA that has a 5' diphosphate group, with GTP, S-adenosylmethionine and a capping enzyme system in an in vitro capping enzyme reaction under conditions and for sufficient time wherein at least a portion of the uncapped RNA is capped. In such embodiments comprising steps (1) through (3), the method is used to obtain RNA that is greater than 80%, greater than 90%, or greater than 95%, capped, even if only a low percentage of the RNA is capped by the capping enzyme system (e.g., if the RNA is "difficult-to-cap"). A variety of capping enzyme systems are known in the art and any capping enzyme system that is capable of adding a cap nucleotide to the RNA can be used in the method. For example, in some embodiments, the capping enzyme system is selected from among a poxvirus capping enzyme, vaccinia capping enzyme, *Saccharomyces cerevisiae* capping enzyme, and SCRIPTCAP™ capping enzyme kit (EPICENTRE).

In some embodiments comprising steps (1) through (3), the capped RNA and the at least one uncapped RNA in the sample provided in step (1) comprises or consists of prokaryotic RNA (e.g., bacterial mRNA) that is capped in vitro using a capping enzyme system.

In some embodiments, the method for obtaining, isolating or purifying the capped RNA that is present in a sample additionally comprises quantifying the amount of the capped RNA in the sample, wherein the method further comprises the substeps of: (1)(a) quantifying the amount of total RNA in the sample; and (4) quantifying the amount of RNA that was not digested in step (3), thereby quantifying the amount of capped RNA in the sample. In some embodiments, the method further comprises quantifying the amount of RNA that was digested in step (3), thereby quantifying the amount of uncapped RNA in the sample. In some embodiments, the RNA is quantified at each step using a method known in the art (e.g., using RIBOGREEN DYE (Invitrogen, Carlsbad Calif.), or by precipitating the RNA with 2.5 M ammonium acetate, or with 0.3 M sodium or potassium acetate and ethanol or isopropanol, resuspending the pellets in water, and quantifying the RNA spectrophotometrically based on the $A_{260}$ extinction coefficient).

In some embodiments of the method for quantifying the capped RNA that is present in a sample, the sample may contain RNA that has a 5' monophosphate group (e.g., 18S and 26S or 28S eukaryotic rRNA, or 16S and 23S prokaryotic rRNA, eukaryotic or viral-encoded miRNA, or introns from RNA that has been spliced or endoribonucleolytically processed). Thus, in some embodiments of the method for quantifying the amount of capped RNA or uncapped RNA in the sample, the sample provided in step (1) additionally comprises RNA that has a 5' monophosphate group and the method further comprises quantifying the amount of RNA that has a 5' monophosphate group in the sample, wherein, prior to step (2) of contacting the sample with the RNA polyphosphatase, the method additionally comprises the sub-steps of: (1)(b) contacting the sample provided in step (1) with the 5' exoribonuclease under conditions and for sufficient time wherein RNA in the sample that has a 5' monophosphate group is digested but capped RNA and RNA that has a 5' polyphosphate group is not digested; and (1)(c) quantifying the amount of RNA that was digested or the amount of RNA that was not digested in step (1)(b), whereby the amount of RNA in the sample that was digested indicates the amount of RNA in the sample that has a 5' monophosphate group.

In some other embodiments of the method for quantifying the capped RNA that is present in a sample wherein the sample may also contain RNA that has a 5' monophosphate group (e.g., 18S and 26S or 28S eukaryotic rRNA, or 16S and 23S prokaryotic rRNA, eukaryotic or viral-encoded miRNA, or introns from RNA that has been spliced or endoribonucleolytically processed), it is desirable to convert RNA that has a 5' monophosphate group to RNA that has a 5' hydroxyl group prior to the 5' exoribonuclease step (e.g., so that the RNA that has a 5' monophosphate group will not be digested by the 5' exoribonuclease, which could complicate quantification of the efficiency of capping of RNA that has a 5' polyphosphate group). Thus, in some embodiments of the method for quantifying the amount of capped RNA or uncapped RNA in the sample, wherein the sample provided in step (1) comprises RNA that has a 5' monophosphate group, prior to step (2) of contacting the sample with the RNA polyphosphatase, the method additionally comprises the sub-steps of: (1)(d) additionally providing an RNA 5' monophosphatase (RMP) (e.g. RMP1, EPICENTRE) in step (1), and (1)(e) contacting the sample provided in step (1) with the RNA 5' monophosphatase under conditions and for sufficient time wherein RNA in the sample that has a 5' monophosphate group is converted to RNA that has a 5' hydroxyl group, whereby the amount of RNA in the sample that is digested by the 5' exoribonuclease in step (3) indicates the amount of RNA in the sample that has a 5' polyphosphate, but does not indicate the amount of RNA in the sample provided in step (1) that has a 5' monophosphate group. In some of these embodiments, the RNA 5' monophosphatase is inactivated or removed prior to step (2). In some other embodiments, the RNA 5' monophosphatase is inactivated by the reaction conditions employed in step (2). In some embodiments the RMP is inactivated or removed immediately following its use in the reaction (e.g., for RMP1, by heating or addition of EDTA or zinc).

The applicants found that the RMP, RNA 5' monophosphatase 1 (EPICENTRE, Madison, Wis.), removed 5'-monophosphate groups from rRNA, including 18S and 26S or 28S eukaryotic rRNA, and 16S and 23S prokaryotic rRNA, and that this enzyme can be used for this purpose. However, the applicants found certain other methods are more efficient than RNA 5' monophosphatase 1 treatment for removing the large amounts of rRNA in most samples (e.g., rRNA comprises about 95 to 98% of the total RNA in most cells). Thus, in some preferred embodiments, the sample that is provided in step (1) for use in the method of the present invention already has the rRNA removed (e.g., using RIBOMINUS™ Kits from Invitrogen Life Technologies). Prior removal of the rRNA using RIBOMINUS or an alternative method so that the sample provided contains substantially less rRNA makes the methods of the present invention more efficient and effective for their intended purposes. Therefore, unless otherwise specifically stated herein, it will be understood that, in some preferred embodiments, 5'-monophosphorylated ribosomal RNA molecules have already been substantially removed from the samples provided in step (1) of a method of the present invention.

For example, in some other preferred embodiments of any of the methods for obtaining, isolating or purifying capped RNA that is present in a sample that also contains uncapped RNA or for additionally quantifying the amount of the capped RNA in the sample and/or quantifying the amount of uncapped RNA in the sample, the sample provided in step (1) is treated to specifically remove only the ribosomal RNA from the sample prior to its use in the method (e.g., using RIBOMINUS™ rRNA removal kits from INVITROGEN, or another suitable method). Removal of the ribosomal RNA from the sample using a protocol such as that for a RIBOMINUS kit facilitates analysis of the other RNA molecules of interest in the sample, including the capped RNA and the uncapped RNA (e.g., the RNA that has a 5' polyphosphate group and the RNA that has a 5'-monophosphate group that is in the sample after removal of the ribosomal RNA.

In some embodiments of the method for obtaining, isolating, purifying or quantifying the capped RNA that is present in a sample, the sample may also contain RNA that has a 5' hydroxyl group (e.g., as a result of digestion by a ribonuclease such as RNase A). RNA that has a 5' hydroxyl group is not digested by 5' exoribonuclease. Thus, in some embodiments of the method for obtaining, isolating, purifying or quantifying the amount of capped RNA in the sample, the sample provided in step (1) additionally comprises RNA that has a 5' hydroxyl group, and the method further comprises the steps of: (1)(f) additionally providing a polynucleotide kinase (e.g., phage T4 polynucleotide kinase) and ATP in step (1); (5) contacting the sample from step (3) with polynucleotide kinase (e.g., phage T4 polynucleotide kinase) and the ATP under conditions and for sufficient time wherein RNA that has a 5' hydroxyl group is phosphorylated to RNA that has a 5' monophosphate group; (6) contacting the sample from step (5) with the 5' exoribonuclease under conditions and for sufficient time wherein RNA that has a 5' monophosphate group is digested, but capped RNA and RNA that has a 5' polyphosphate group and RNA that has a 5' hydroxyl group are not digested, and obtaining isolating, purifying and/or quantifying the capped RNA.

In some embodiments, the method further comprises quantifying the amount of RNA that has a 5' hydroxyl group in the sample, wherein the method further comprises: (7) quantifying the amount of RNA that was digested or the amount of RNA that was not digested in step (6), whereby the amount of RNA in the sample that was digested indicates the amount of RNA in the sample that has a 5' hydroxyl group.

Those with knowledge in the art will understand that the order of performing certain steps of the various methods of the invention is important, but that the order of the steps can be varied provided that the effects of each of the enzymes on the groups at the 5'-ends of the various classes of RNA molecules that may be present in the sample are carefully taken into account so as not to adversely affect the intended goal.

Another embodiment of the invention is a kit for obtaining, isolating or purifying capped RNA that is present in a sample or for quantifying its amount, the kit comprising: (1) an RNA polyphosphatase (RPP) (e.g., selected from the group consisting of an aluminum-inducible RPP, *E. coli* RPP I, and *Shigella* RPP I); and (2) a 5' exoribonuclease (XRN) (e.g., selected from the group consisting of TERMINATOR™ 5'-phosphate-dependent exonuclease and *Saccharomyces cerevisae* Xrn I exoribonuclease (Xrn I)). In some embodiments the kit additionally comprises a polynucleotide kinase (PNK) (e.g., T4 PNK). In some other embodiments, the kit additionally comprises an RNA 5' monophosphatase (e.g., RNA 5' monophosphatase 1, EPICENTRE).

Still another embodiment of invention is a composition comprising an RNA polyphosphatase that is conjugated to an affinity binding molecule. In some embodiments the affinity binding molecule is an analyte-binding substance (ABS) that is capable of specific binding with an analyte. In some embodiments, the affinity binding molecule is selected from the group comprising or consisting of: (a) a nucleic acid comprising DNA or RNA; (b) a protein; (c) a glycoprotein; (d) a lipoprotein; (e) a carbohydrate; (f) a lipid; (g) a lectin; (h) a hormone; (i) a hormone receptor; (j) biotin; (k) avidin or streptavidin; (l) protein A; (m) protein G; (n) an antibody; (o) an antigen; and (p) digoxigenin.

Affinity binding molecules, including analyte-binding substances and their analytes, can be any substances that form a specific binding pair which can be used in a method of the invention. In some embodiments, the analyte is a cellular small biochemical molecule (e.g., selected from among a steroid or other hormone, a vitamin, or a cellular metabolite) or a macromolecule (e.g., selected from among a nucleic acid, a protein, a lipid, or a carbohydrate). In some embodiments, the analyte is conjugated to a small molecule (e.g., selected from among biotin, digoxigenin, or a visible, fluorescent, or chemiluminescent dye). In some embodiments, the ABS is a small biochemical molecule (e.g., selected from among biotin and digoxigenin) or a macromolecule (e.g., selected from among a nucleic acid and a protein (e.g., selected from among streptavidin, protein A, an antibody, and a hormone receptor). An ABS that is a macromolecule can be conjugated to a small biochemical molecule (e.g., selected from among biotin, digoxigenin, a visible dye, a fluorescent dye, and a chemiluminescent dye).

Another embodiment of the invention is a method for labeling an affinity binding molecule (e.g., an analyte-binding substance), the method comprising the steps of: (i) providing: RNA polyphosphatase; an affinity binding molecule (e.g., an analyte-binding substance); and a chemical conjugation reagent; and (ii) contacting the RNA polyphosphatase with the affinity binding molecule and the chemical conjugation reagent under conditions wherein the RNA polyphosphatase is joined to the affinity binding molecule, wherein the enzymatic activity of the RNA polyphosphatase and the ability of the affinity binding molecule to form a specific binding pair are retained. In some embodiments, the affinity binding molecule is selected from the group consisting of a nucleic acid probe, a protein, streptavidin, biotin, protein A, an antibody, an artificial antibody, an aptamer selected using SELEX, and digoxigenin. Since the RPPs of the invention are useful for making conjugates with affinity binding molecules that are used as signal-amplifying substances for sensitive detection of nucleic acids, proteins, or other analytes in the absence of divalent metal ions.

Another embodiment of the invention is a method for preparing a signal-amplifying substance consisting of RNA polyphosphatase that is conjugated or bound to an affinity binding molecule, the method comprising the steps of: (a) providing: a reactive affinity binding molecule consisting of an affinity binding molecule with a reactive moiety; and RNA polyphosphatase; and (b) contacting the reactive affinity binding molecule with the RNA polyphosphatase under conditions wherein the reactive affinity binding molecule is covalently joined to the RNA polyphosphatase, wherein the enzymatic activity of the RNA polyphosphatase and the ability of the affinity binding molecule to form a specific binding pair are retained. In some embodiments, the affinity binding molecule is selected from the group consisting of a nucleic acid probe, a protein, streptavidin, biotin, protein A, an antibody, an artificial antibody, an aptamer selected using SELEX, and digoxigenin. Thus, the RPPs of the invention are useful for making conjugates with small molecules like biotin or digoxigenin and with nucleic acids or proteins (e.g., streptavidin, protein A, or primary or secondary antibodies) for use as signal-amplifying substances for sensitive detection of nucleic acids, proteins, and other analytes.

Since the RPPs of the invention are single-subunit enzymes, they are useful for genetically engineering fusion proteins consisting of the RPP enzyme and a protein affinity-binding molecule for use as signal-amplifying substances. Thus, still another embodiment of invention is a composition comprising a recombinant fusion protein consisting of an RNA polyphosphatase (RPP) (e.g., selected from the group consisting of an aluminum-inducible RPP, *E. coli* RPP I, and *Shigella* RPP I) and a protein that is an analyte-binding substance (ABS) (e.g., selected from the group consisting of streptavidin, a single-chain artificial antibody, and protein A). A fusion protein is made by making a recombinant nucleic acid consisting of the nucleic acid sequence that encodes the RPP joined to the 5' end or the 3' end of the nucleic acid sequence that encodes the ABS, then cloning the recombinant nucleic into an expression vector (e.g., a plasmid) downstream of a conditionally inducible promoter sequence (e.g., a T7-type promoter) to make a recombinant vector, then transforming a host cell that is capable of conditionally expressing the recombinant nucleic acid to obtain a recombinant host cell, growing the recombinant host cell under conditions wherein the recombinant fusion protein is expressed, and purifying the recombinant fusion protein.

Thus, the RPPs of the invention can be used in a multiplicity of ways for making signal-amplifying substances for use in methods for detection of biomolecules for research, molecular diagnostics, immunodiagnostics, and other applications.

DEFINITIONS

The present invention will be understood and interpreted based on the definitions of terms as defined below.

When the terms "for example", "e.g.", "such as", "include", "including" or variations thereof are used herein, these terms will not be deemed to be terms of limitation, and will be interpreted to mean "but not limited to" or "without limitation."

An "acceptor oligonucleotide", as used herein, means an oligonucleotide that has a 3' hydroxyl group that is capable of being joined to the 5' end of an RNA that has a 5' phosphate group by the action of an RNA ligase, wherein the RNA that has a 5' phosphate group is referred to as the "donor." An acceptor oligonucleotide that consists of ribonucleotides is as an "RNA acceptor oligonucleotide" or an "RNA acceptor."

"Affinity binding molecules" or a "specific binding pair" herein means two molecules that have affinity for and "bind" to each other with specificity under certain conditions, referred to as "binding conditions." Each of the two molecules comprising the specific binding pair is an "affinity binding molecule." Biotin and streptavidin or avidin are examples of "affinity binding molecules" or "specific binding pairs," each of which is an "affinity binding molecule."

An "analyte" means a substance whose presence, concentration, or amount in a sample is being determined in an assay or method. An "analyte-binding substance" (or "ABS") is a substance that binds an analyte with specificity. As used herein, an analyte and an ABS that binds it with specificity comprise a "specific binding pair," and the analyte and the ABS are each "affinity binding molecules." Any of the methods or assays of the invention can use multiple specific binding pairs (including analytes, analyte-binding substances, or other affinity binding molecules) for detecting, capturing, or quantifying one or more analytes in a sample (e.g., using sandwich assay methods and compositions known in the art).

The invention is not limited to any specific affinity binding molecule, specific binding pair, analyte, or analyte-binding substance. Affinity binding molecules, analytes, and analyte-binding substances include, for example: proteins, including glycoproteins and lipoproteins, enzymes, hormones, receptors, antigens and antibodies; nucleic acids (e.g., DNA or RNA); segments of nucleic acids; biochemical molecules; and polysaccharides. An analyte is often associated with a biological entity that is present in a sample if and only if the analyte is present. Many other analytes will be apparent to those skilled in the art.

In the case of immunoassays that entail the use of two antibodies, in some embodiments, the analyte is an antigen conjugated or bound to first antibody (in the case of a sandwich assay) or a first antibody conjugated or bound to antigen (in the case of an immunosorbent assay); and the ABS is the second antibody, which in turn, is conjugated or bound to RNA polyphosphatase as a signal-amplifying substance. In the case of nucleic acid assays, in some embodiments, the analyte is a nucleic acid molecule or a portion of a nucleic acid molecule (e.g., a portion which exhibits a particular sequence) and the ABS is another nucleic acid molecule that is complementary to the analyte. The nucleic acid that is the ABS (e.g., a nucleic acid probe), in turn, is conjugated to a first affinity binding molecule (e.g., biotin or digoxigenin), and the ABS or the nucleic acid probe is detected using a second affinity binding molecule (e.g., streptavidin or an antibody that binds digoxigenin, respectively) that binds a third affinity binding molecule, which, in turn, is conjugated or bound to RNA polyphosphatase as a signal-amplifying substance.

In some embodiments, RNA polyphosphatase is conjugated to an affinity binding molecule for use as a signal-amplifying substance using methods known in the art. For example, in some embodiments, RNA polyphosphatase is conjugated to a macromolecular affinity binding molecule, (e.g., an analyte-binding substance, e.g., an antibody, streptavidin, protein A, a nucleic acid, or another affinity binding molecule) using reagents and methods as described in: "BIO-CONJUGATE Techniques", by Greg T. Hermanson, Published by Academic Press, Inc., San Diego, Calif., 1996. In other embodiments, the affinity binding molecule (e.g., analyte-binding substance) is conjugated to a solid surface. In still other embodiments, RNA polyphosphatase is conjugated to an affinity binding molecule (e.g., biotin or digoxigenin) for use as a signal-amplifying substance using methods known in the art. For example, in some embodiments, biotin or another small affinity molecule is conjugated to RNA polyphosphatase using a biotinylation reagents and methods as described in "Avidin-Biotin Chemistry: A Handbook", by D. Savage et al., Pierce Chemical Company, 1992 and in "Handbook of Fluorescent Probes and Research Products", Ninth Edition, by R. P. Hoagland, Molecular Probes, Inc.

Affinity binding molecules that are conjugated to DNA or RNA can also be synthesized using an oligonucleotide synthesizer using reagents and methods known in the art. Thus, in some embodiments, a first affinity binding molecule (e.g., biotin or digoxigenin) is conjugated to other molecules (e.g., to RNA or DNA) and a second affinity binding molecule (e.g., streptavidin or avidin, which bind biotin, or a specific antibody that binds digoxigenin) is covalently conjugated or non-covalently bound to a solid surface using any of the methods known in the art.

A preferred analyte-binding substance is a nucleic acid or a polynucleotide or an oligonucleotide or a segment of a nucleic acid or polynucleotide, including nucleic acids composed of DNA, RNA, or both DNA and RNA mononucleosides, including modified DNA or RNA mononucleosides. When an analyte-binding substance comprising a nucleic acid is used, a preferred analyte of the invention is a nucleic acid, polynucleotide or oligonucleotide which has a segment or region that is at least partially complementary with at least a segment or region of the analyte-binding substance. Such nucleic acid affinity binding molecules can be made by any of numerous known in vivo or in vitro techniques, including automated nucleic acid synthesis techniques, PCR, or in vitro transcription. As understood in the art, the length that a DNA or RNA affinity binding molecule must have to provide a pre-determined specificity in an assay will depend in part on the amount and complexity of nucleic acid in the sample being assayed. Such an affinity binding molecule will usually require at least five nucleotides. In some embodiments, a method termed "SELEX," as described by Gold and Tuerk in U.S. Pat. No. 5,270,163, is used to select a nucleic acid for use as an analyte-binding substance according to the invention. SELEX permits selection of a nucleic acid molecule that has high affinity for a specific analyte from a large population of nucleic acid molecules, at least a portion of which have a randomized sequence. For example, a population of all possible randomized 25-mer oligonucleotides (i.e., having each of four possible nucleic acid bases at every position) will contain $4^{25}$ (or $10^{15}$) different nucleic acid molecules, each of which has a different three-dimensional structure and different analyte binding properties. In some embodiments, SELEX is used, for example according to the methods described in U.S. Pat. Nos. 5,270,163; 5,567,588; 5,580,737; 5,587,468; 5,683,867; 5,696,249; 5,723,594; 5,773,598; 5,817,785; 5,861,254; 5,958,691; 5,998,142; 6,001,577; 6,013,443; and 6,030,776, in order to select an analyte-binding substance that consists of a nucleic acid that has high affinity for a specific analyte that is not a nucleic acid or polynucleotide (e.g., a protein analyte, such as an antibody, enzyme, or the like). Once selected using SELEX, nucleic acid affinity binding molecules can be made by any of numerous known in vivo or in vitro techniques, including automated nucleic acid synthesis techniques, PCR, or in vitro transcription.

From the description of analyte and an analyte-binding substance, it is apparent that the present invention has widespread applicability, including in applications in which immunoassays or nucleic acid probe hybridization assays are employed. Thus, among other applications, the invention is useful in diagnosing diseases in plants and animals, including humans; and in testing products, such as food, blood, and tissue cultures, for contaminants.

The term "binding" according to the invention refers to the interaction between the affinity binding molecules or specific binding pair (e.g. between one affinity binding molecule and another affinity binding molecule, such as between an analyte and its analyte-binding substance) as a result of non-covalent bonds, such as hydrogen bonds, hydrophobic interactions, van der Waals bonds, and ionic bonds. Without being bound by theory, it is believed in the art that these kinds of non-covalent bonds result in binding, in part due to complementary shapes or structures of the molecules involved in the specific binding pair. Based on the definition for "binding," and the wide variety of affinity binding molecules or specific binding pairs, it is clear that binding conditions vary for different specific binding pairs. Those skilled in the art can easily find or determine conditions whereby, in a sample, binding occurs between the affinity binding molecules. In particular, those skilled in the art can easily determine conditions whereby binding between affinity binding molecules that would be considered in the art to be "specific binding" can be made to occur. As understood in the art, such specificity is usually due to the higher affinity between the affinity binding molecules than for other substances and components (e.g., vessel walls, solid supports) in a sample. In certain cases, the specificity might also involve, or might be due to, a significantly more rapid association of affinity binding molecules than with other substances and components in a sample.

As used herein, the terms "buffer" or "buffering agents" refer to materials that when added to a solution, cause the solution to resist changes in pH. As used herein, the term "reaction buffer" refers to a buffering solution in which an enzymatic reaction is performed. As used herein, the term "storage buffer" refers to a buffering solution in which an enzyme is stored.

A "cap" or a "cap nucleotide" is a guanine nucleotide that is joined through its 5' end to the 5' end of a primary RNA transcript. The RNA that has the cap nucleotide joined to its 5' end is referred to as "capped RNA" or "capped RNA transcript" or "capped transcript." A common cap nucleoside is 7-methylguanosine or $N^7$-methylguanosine (sometimes referred to as "standard cap"), which has a structure designated as "$m^7G$," in which case the capped RNA or "$m^7G$-capped RNA" has a structure designated as $m^7G(5')ppp(5')N_1(pN)_x$-OH(3'), or more simply, as $m^7GpppN_1(pN)_x$ or $m^7G[5']ppp[5']N$, wherein $m^7G$ represents the 7-methylguanosine cap nucleoside, ppp represents the triphosphate bridge between the 5' carbons of the cap nucleoside and the first nucleotide of the primary RNA transcript, $N_1(pN)_x$-OH(3') represents the primary RNA transcript, of which $N_1$ is the most 5'-nucleotide, "p" represents a phosphate group, "G" represents a guanosine nucleoside, "$m^7$" represents the methyl group on the 7-position of guanine, and "[5']" indicates the position at which the "p" is joined to the ribose of the cap nucleotide and the first nucleoside of the mRNA transcript ("N"). In addition to this "standard cap," a variety of other naturally-occurring and synthetic cap analogs are known in the art. RNA that has any cap nucleotide is referred to as "capped RNA." In some embodiments, the capped RNA is naturally occurring from a biological sample. In some embodiments, the capped RNA is obtained by in vitro capping of RNA that has a 5' triphosphate group or RNA that has a 5' diphosphate group with a capping enzyme system (e.g., vaccinia capping enzyme system or *Saccharomyces cerevisiae* capping enzyme system). Alternatively, in some embodiments, the capped RNA is obtained by in vitro transcription (IVT) of a DNA template that contains an RNA polymerase promoter, wherein, in addition to the GTP, the IVT reaction also contains a dinucleotide cap analog (e.g., selected from among a $m^7$ GpppG cap analog; an $N^7$-methyl, 2'-O-methyl-GpppG ARCA cap analog; and an $N^7$-methyl, 3'-O-methyl-GpppG ARCA cap analog) using methods known in the art (e.g., using an AMPLICAP™ T7 capping kit (EPICENTRE)).

In vivo, capping of a 5'-triphosphorylated primary mRNA transcript occurs via several enzymatic steps (e.g., see Martin, S A et al., J. Biol. Chem. 250: 9322, 1975; Myette, J R and Niles, E G, J. Biol. Chem. 271: 11936, 1996; M A Higman, et al., J. Biol. Chem. 267: 16430, 1992).

The following enzymatic reactions are involved in capping of eukaryotic mRNA:

(1) RNA triphosphatase cleaves the 5'-triphosphate of mRNA to a diphosphate, $pppN_1(p)N_x$-OH(3')→$ppN_1(pN)_x$-OH(3')+Pi; and then (2) RNA guanyltransferase catalyzes joining of GTP to the 5'-diphosphate of the most 5' nucleotide ($N_1$) of the mRNA, $ppN_1(pN)_x$-OH(3')+GTP→$G(5')ppp(5')N_1(pN)_x$-OH(3')+PPi; and finally, (3) guanine-7-methyltransferase, using S-adenosyl-methionine (AdoMet) as a co-factor, catalyzes methylation of the 7-nitrogen of guanine in the cap nucleotide,
$G(5')ppp(5')N_1(pN)_x$-OH(3')+AdoMet→$m^7G(5')ppp(5')N_1(pN)_x$-OH(3')+AdoHyc.

RNA that results from the action of the RNA triphosphatase and the RNA guanyltransferase enzymatic activities, as well as RNA that is additionally methylated by the guanine-7-methyltransferase enzymatic activity, is referred to herein as "5' capped RNA" or "capped RNA", and a "capping enzyme system" or, more simply, a "capping enzyme" herein means any combination of one or more polypeptides having the enzymatic activities that result in "capped RNA." Capping enzyme systems, including cloned forms of such enzymes, have been identified and purified from many sources and are well known in the art (e.g., see Shuman, S, Prog. Nucleic Acid Res. Mol. Biol. 66: 1-40, 2001; Shuman, S, Prog Nucleic Acid Res Mol Biol 50: 101-129, 1995; Shuman, S et al., J. Biol. Chem. 255: 11588, 1980; Banerjee, A K, Microbiol. Rev. 44: 175-205, 1980; Wang, S P et al., Proc. Natl. Acad. Sci. USA 94: 9573, 1997; Higman M. A. et al., J. Biol. Chem. 267: 16430, 1992; Higman, M A et al., J. Biol. Chem. 269: 14974-14981, 1994; Myette, J R and Niles, E G, J. Biol. Chem. 271: 11936-11944, 1996). Any capping enzyme system that can convert uncapped RNA that has a 5' polyphosphate to capped RNA can be used to provide a capped RNA for any of the embodiments of the present invention. In some embodiments, the capping enzyme system is a poxvirus capping enzyme system. In some preferred embodiments, the capping enzyme system is vaccinia virus capping enzyme. In some embodiments, the capping enzyme system is *Saccharomyces cerevisiae* capping enzyme. Also, in view of the fact that genes encoding RNA triphosphatase, RNA guanyltransferase and guanine-7-methyltransferase from one source can complement deletions in one or all of these genes from another source, the capping enzyme system can originate from one source, or one or more of the RNA triphosphatase, RNA guanyltransferase, and/or guanine-7-methyltransferase activities can comprise a polypeptide from a different source.

As used herein, the terms "chelator" or "chelating agent" refer to any materials having more than one atom with a lone pair of electrons that are available to bond to a metal cation. EDTA is one example of a chelator or chelating agent that can be used herein. As used herein, the term "divalent salt" or "divalent metal cation" refers to any salt in which a metal (e.g., Mg, Mn, Co, Ca, or Sr) has a net 2+ charge in solution.

A "decapping enzyme" means herein a Dcp1/Dcp2 complex decapping enzyme (or "Dcp2-type decapping enzyme") that converts a capped RNA to an RNA that has a 5' monophosphate group under conditions wherein it does not convert RNA that has a 5' polyphosphate group to RNA that has a 5' monophosphate group. A "Dcp2-type decapping enzyme" herein means a decapping enzyme that is a member of the Nudix superfamily of enzymes, which enzymes share a conserved amino acid sequence called the Nudix (or MutT) motif or Nudix box, exhibiting the sequence GX$_5$EX$_7$REUXEEXGU (Dunckley, T. and Parker, R. EMBO J. 18: 5411-5422, 1999; van Dijk, E et al., EMBO J. 21: 6915-6924, 2002; Steiger, M et al., RNA 9: 231-238, 2003; Xu, W et al. J. Biol. Chem. 279: 24861-24865, 2004; Gunawardana, D et al., Nucleic Acids Res. 36: 203-216, 2008).

As used herein, the term "enzyme" refers to protein molecules or protein molecule aggregates that are responsible for catalyzing chemical and biological reactions. One important class of enzymes discovered by the applicants comprises or consists of RNA 5' polyphosphatases, which enzymes convert RNA that has a 5' polyphosphate group, but not capped RNA, to RNA that has a 5' monophosphate group. However, other enzymes are also used in various methods and kits of the invention. In general, a method or kit of the invention is not limited to use of a particular enzyme from a particular source. Rather, a method or kit of the present invention comprises any enzyme from any source that has an equivalent enzymatic activity to the particular enzyme disclosed herein with respect to the particular method or kit. For example, in some embodiments, an RNA 5' polyphosphatase in a method or kit is selected from among *Escherichia coli* or *Shigella* RNA 5' polyphosphatase I, and another RNA 5' polyphosphatase enzyme that converts RNA that has a 5' polyphosphate group, but not capped RNA, to RNA that has a 5' monophosphate group; a 5' exoribonuclease (XRN) in a method or kit is selected from among *Saccharomyces cerevisiae* Xrn I exoribonuclease, TERMINATOR™ 5'-phosphate-dependent exonuclease (EPICENTRE) and another enzyme that digests 5'-monophosphorylated RNA to mononucleotides, but it generally does not digest RNA that has a 5' triphosphate, 5' cap, or 5' hydroxyl group; a polynucleotide kinase (PNK) in a method or kit is selected from among T4 polynucleotide kinase, and any other enzyme that can transfer a monophosphate group from ATP or another nucleoside-5'-triphosphate to the 5' end of RNA that has a 5' hydroxyl group under suitable reaction conditions; and an RNA monophosphatase in a method or kit is selected from among RNA 5' monophosphatase 1 (EPICENTRE, Madison, Wis., USA) (e.g., used according to the instructions of the manufacturer, and any other RNA monophosphatase that converts RNA that has a 5' monophosphate group to RNA that has a 5' hydroxyl group under conditions wherein said RNA 5' monophosphatase does not substantially digest RNA that has a 5' triphosphate group to an RNA that has a 5' hydroxyl group.

The methods, buffers, and reaction conditions presented herein or provided in commercially available products, including in the examples, are presently preferred for the embodiments of the methods, compositions, and kits of the present invention. However, other enzyme storage buffers, reaction buffers, and reaction conditions known in the art are used in other embodiments of the present invention.

As used herein, "5' exoribonuclease" ("XRN") means a 5' exonuclease that has greater than 20-fold more 5'-to-3' exonuclease activity for a single-stranded RNA substrate that has a 5'-monophosphorylated terminus than for the same RNA substrate that has a 5'-triphosphorylated or 5'-capped terminus. Enzyme activity of a 5' exoribonuclease of the invention can be measured using a number of different methods. A suitable method for assaying activity and determining relative activity using RNA substrates with a 5'-triphosphate, a 5'-cap, or a 5'-monophosphate is described by Stevens and Poole (J. Biol. Chem., 270: 16063, 1995). One preferred composition of 5' exoribonuclease is *Saccharomyces cerevisiae* Xrn1p/5' exoribonuclease 1 (or "Xrn I exoribonuclease" or "Xrn 15' exoribonuclease" or "5' Xrnlp exoribonuclease") (e.g., prepared using methods known in the art. In some embodiments, 5' exoribonuclease is obtained by expression of the *Saccharomyces cerevisiae* XRN1 gene that has been cloned in a plasmid, and then replicated and expressed in *Escherichia coli* cells. One preferred 5' exoribonuclease is TERMINATOR™ 5'-phosphate-dependent exonuclease (EPICENTRE, Madison, Wis., USA) (e.g., used according to the instructions of the manufacturer.

The term "isolated" or "purified" when used in relation to a nucleic acid, as in "isolated or purified polynucleotide" or "isolated or purified oligonucleotide" or "isolated or purified RNA" refers to one or more nucleic acid molecules that have a common property (e.g., molecules that have the same chemical moiety or group on their 5' ends) that are separated from at least one contaminant with which it or they are ordinarily associated in its or their source. Thus, an isolated or purified nucleic acid is present in a form or setting that is different from that in which it is found in nature. In contrast, non-isolated or non-purified nucleic acids (e.g., DNA and RNA) are found in the state they exist in nature. For example, a given RNA molecule or molecules that share a common property (e.g., capped RNA molecules) are found in the cell as a mixture with numerous other RNA molecules (e.g., rRNA, ncRNA, miRNA, snRNA, degraded RNA).

"Nucleoside", as used herein, refers to a compound consisting of a guanine (G) or adenine (A) purine or a thymine (T), uridine (U), or cytidine (C) pyrimidine base that is covalently linked to a pentose sugar, whereas "nucleotide" refers to a nucleoside that is phosphorylated at one of the hydroxyl groups of the pentose sugar.

A "nucleic acid" or a "polynucleotide", as used herein, is a covalently linked sequence of nucleotides in which the 3' position of the sugar moiety of one nucleotide is joined by a phosphodiester group to the 5' position of the sugar moiety of the next nucleotide, and in which the nucleotide residues (bases) are linked in specific sequence; i.e., a linear order of nucleotides. An "oligonucleotide", as used herein, is a short polynucleotide or a portion of a polynucleotide. An oligonucleotide typically contains a sequence of about two to about one hundred bases, although longer molecules may also sometimes be referred to as oligonucleotides. The word "oligo" is sometimes used in place of the word "oligonucleotide". In some embodiments, the oligonucleotide consists of 2'-deoxyribonucleotides (DNA). In some embodiments, the oligonucleotide consists of ribonucleotides (RNA). In some embodiments, the oligonucleotide consists of both DNA and RNA.

Linear nucleic acid molecules are said to have a "5' end" (or "5'-terminus") and a "3' end" (or "3'-terminus") because, except with respect to a cap (as described elsewhere herein), mononucleotides are joined in one direction via a phosphodiester linkage to make oligonucleotides, in a manner such that a phosphate on the 5'-carbon of one mononucleotide sugar moiety is joined to an oxygen on the 3'-carbon of the sugar moiety of its neighboring mononucleotide. Therefore, an end of an oligonucleotide referred to as the "5' end" if its 5' phosphate is not linked to the oxygen of the 3'-carbon of a mononucleotide sugar moiety and as the "3' end" if its 3' oxygen is not linked to a 5' phosphate of the sugar moiety of a subsequent mononucleotide.

With respect to nucleic acids, or oligonucleotides, or polynucleotides, the terms "complementary" or "complementarity" are used herein in reference to a sequence of nucleotides related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon hybridization of nucleic acids.

The term "homology" refers to a degree of complementarity of one nucleic acid sequence with another nucleic acid sequence. There may be partial homology or complete homology (i.e., complementarity). A partially complementary sequence is one that at least partially inhibits a completely complementary sequence from hybridizing to a target nucleic acid and is referred to using the functional term "substantially homologous." For example, in some embodiments of the present invention, the RNA 5' polyphosphatase comprises or consists of an enzyme that is substantially homologous to SEQ ID NO: 1. In some embodiments, the RNA 5' polyphosphatase is at least 70% homologous to SEQ ID NO: 1. In some embodiments, the RNA 5' polyphosphatase is at least 80% homologous to SEQ ID NO: 1. In some embodiments, the RNA 5' polyphosphatase is at least 90% homologous to SEQ ID NO: 1. In some embodiments, the RNA 5' polyphosphatase is at least 95% homologous to SEQ ID NO: 1. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks complementarity or that has only a low degree of complementarity (e.g., less than about 30% complementarity). In the case in which specific binding is low or non-existent, the probe will not hybridize to a nucleic acid target. When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein. As used herein, the terms "hybridization" or "annealing" are used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved affected by such conditions as the concentration of salts, the $T_m$ (melting temperature) of the formed hybrid, the presence of other components (e.g., the presence or absence of polyethylene glycol or betaine), the molarity of the hybridizing strands and the G:C content of the nucleic acid strands. In general, when a first nucleic acid is said to be complementary to a second nucleic acid herein (e.g., when an mRNA is complementary to a gene that exhibits a particular sequence), it means that the first nucleic acid has sufficient complementarity or homology with the second nucleic acid so that it anneals to the second nucleic acid under conditions of high stringency. However, in some embodiments, the first nucleic acid has sufficient complementarity or homology with the second nucleic acid so that it anneals to the second nucleic acid under conditions of moderate stringency, meaning that the stringency is between low stringency and high stringency. Those with knowledge in the art will know how to make conditions of moderate or high stringency.

An "oligo cap" or "oligonucleotide cap" is an acceptor oligonucleotide that is joined to the 5' end of a 5'-monophosphorylated RNA molecule by the action of RNA ligase as part of an "oligo capping" method. An "oligo cap" differs from an "$m^7G$ cap" that is typically found on eukaryotic mRNA molecules. The cap on eukaryotic mRNA (e.g., $m^7G$ cap) and some other eukaryotic RNA molecules is sometimes referred to herein as an "$m^7G$-cap" or a "cap nucleotide" or a "nucleotide cap" to distinguish it from an "oligonucleotide cap" or an "oligo cap." We sometimes refer to the cap nucleotide of eukaryotic mRNA herein as "$m^7G$-capped RNA", even though the cap nucleotide may have other modifications besides the N7-methyl group of the guanine base.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue.

A "primary RNA" or "primary RNA transcript" means an RNA molecule that is synthesized by an RNA polymerase in vivo or in vitro and which RNA molecule has a triphosphate on the 5'-carbon of its most 5' nucleotide.

"RNA amplification" or an "RNA amplification reaction" according to the present invention is a method that that results in synthesis of an RNA product wherein there is an increase in the number of copies of an RNA sequence or its complementary sequence compared to the number of copies of the sequence present in a sample. For example, in some embodiments, a RIBOMULTIPLIER™ sense RNA amplification kit (EPICENTRE) is used to generate sense RNA from pre-existing RNA in a sample. Alternatively, in some embodiments, a method that uses an oligo(dT) promoter primer as a first-strand cDNA synthesis primer is used for synthesis of antisense RNA (aRNA) as described by Van Gelder, R. N., et al. (Proc. Natl. Acad. Sci. USA 87: 1663, 1990). In some embodiments, commercially available kits for generating amplified antisense RNA are used (e.g., TARGETAMP™ aRNA Amplification Kits, EPICENTRE, Madison, Wis.). Alternatively, in some embodiments, a second-strand cDNA synthesis primer (or a PCR primer) that exhibits, in its 5' portion, a sequence for one strand of an RNA polymerase promoter and, in its 3' portion, a sequence that is complementary to a sequence exhibited by a tag that is on the 3' end of the first-strand cDNA is used in an RNA amplification method for synthesizing sense RNA. In this embodiment, an RNA acceptor oligonucleotide is ligated to the 5' end of RNA of interest comprising RNA that has a 5' monophosphate group, thereby obtaining 5'-ligation-tagged RNA, which is then used as a template for synthesis of the first-strand cDNA using an RNA-dependent DNA polymerase. Then, double-stranded cDNA that contains the RNA polymerase promoter is synthesized using a DNA polymerase and the second-strand cDNA synthesis primer (or a PCR primer). Finally, amplified sense RNA is synthesized by in vitro transcription of the double-stranded cDNA using an RNA polymerase that binds and initiates transcription from the RNA polymerase promoter. If the RNA of interest in the sample does not already have 5' monophosphate group, it is converted to RNA that has a 5' monophosphate group (e.g., using tobacco acid pyrophosphatase to convert RNA of interest comprising both capped RNA and RNA that has a 5' polyphosphate group, or using an RNA polyphosphatase to convert only RNA that has a 5' polyphosphate group).

The present invention is also not limited to RNA amplification methods that require synthesis of double-stranded cDNA. For example, the present invention also comprises RNA amplification methods and compositions as described in U.S. Patent Appln. No. 2004/0171041 that use an RNA polymerase that can synthesize RNA using single-stranded templates that are functionally joined to a single-stranded promoter, such as methods that use MINI-V RNA polymerase (available from EPICENTRE in the MINI-V™ In Vitro Transcription Kit); in these embodiments, a single-stranded promoter is joined to either the 5' end of the cDNA or the 3'-end of cDNA that is made by reverse transcription of mRNA using an RNA-dependent DNA polymerase to extend a primer, resulting in synthesis of amplified antisense RNA or amplified sense RNA, respectively, by subsequent in vitro transcription of single-stranded DNA templates (e.g., using MINIV RNA polymerase).

An "RNA ligase" means an enzyme or composition of enzyme that catalyzes the joining of RNA that has an hydroxyl group on its 3' end (i.e., an RNA acceptor) to an RNA that has a phosphate group on its 5' end (i.e., an RNA donor). For example, in some embodiments, the RNA ligase is a polypeptide (gp63) encoded by bacteriophage T4 gene 63; this enzyme, which is commonly referred to simply as "T4 RNA ligase," is more correctly now called "T4 RNA ligase 1" since Ho, C K and Shuman, S (Proc. Natl. Acad. Sci. USA 99: 12709-12714, 2002) described a second RNA ligase (gp24.1) that is encoded by bacteriophage T4 gene 24.1, which is now called "T4 RNA ligase 2." Unless otherwise stated, when "T4 RNA ligase" is used in the present specification, we mean T4 RNA ligase 1. For example, in some other embodiments, the RNA ligase is a polypeptide derived from or encoded by an RNA ligase gene from bacteriophage TS2126, which infects *Thermus scotoductus*, including the native phage enzyme and other polypeptides encoded by the nucleic acids as disclosed in U.S. Pat. No. 7,303,901 (i.e., bacteriophage TS2126 RNA ligase).

As defined herein, "RNA 5' monophosphatase" or "RNA 5' monophosphatase enzyme" or "RNA 5' monophosphatase composition" or "RMP" means an enzyme or composition of enzyme that is capable of converting RNA that has a 5' monophosphate group to RNA that has a 5' hydroxyl group under conditions wherein said RNA 5' monophosphatase does not substantially digest uncapped primary RNA (meaning RNA that has a 5' triphosphate group) to an RNA that has a 5' hydroxyl group. Although RNA 5' monophosphatase is defined herein with respect to its capability of digesting a 5' monophosphate group of RNA to a 5' hydroxyl group, the RNA 5' monophosphatase can also have other enzymatic activities. For example, it will be understood herein that a RNA 5' monophosphatase may (but need not) also have enzymatic activity in removing a 3' monophosphate group from RNA that has a 3' monophosphate group. In addition, RNA 5' monophosphatase may (but need not) also be capable of cleaving a monophosphate group from the 5' end of DNA, a ribonucleotide, or a deoxyribonucleotide, and it may even have activity in cleaving a monophosphate group from a non-nucleic acid substrate. In some embodiments of methods or kits of the present invention, the RNA 5' monophosphatase is RNA 5' monophosphatase 1 (RMP1) (EPICENTRE, Madison, Wis., USA) (e.g., used according to the instructions of the manufacturer. The invention is not limited to embodiments comprising RMP1, and any RNA 5' monophosphatase can be used so long as the enzyme functions for its intended purpose of specifically converting RNA that has a 5' monophosphate group to RNA that has a 5' hydroxyl group without converting RNA that has a 5' triphosphate group that is present in the same reaction mixture to an RNA that has a 5' hydroxyl group.

The enzymatic activity of RNA 5' monophosphatase can be defined in various ways using different substrates (e.g., p-nitrophenyl phosphate, an NMP or RNA that has a 5' monophosphate group), conditions, and assays. For example, one unit definition that can be used is: "one unit of RNA 5' monophosphatase is the amount of enzyme that dephosphorylates one micromole of p-nitrophenyl phosphate in one minute at 25° C. in 1M diethanoloamine buffer, pH 9.8, that contains 15 mM p-nitrophenyl phosphate, and 5 mM calcium chloride." For example, one other unit definition that can be used is: "one molecular biology unit (MBU) of RNA 5' monophosphatase (e.g., RNA 5' monophosphatase 1 (RMP1), EPICENTRE) is the amount of enzyme that removes the 5' monophosphate group from one microgram of a defined preparation of a nucleic acid substrate that has a 5'-monophosphate group (e.g., for RMP1, a RNA or DNA substrate, e.g., a defined preparation of 16S and/or 23S bacterial ribosomal RNA or a defined DNA that has a 5' monophosphate group) in 60 minutes at 30° C. in a suitable reaction buffer (e.g., for RMP1, one suitable reaction buffer comprises: 33 mM Tris-acetate, pH 7.5, 66 mM potassium acetate, 10 mM magnesium acetate, 5 mM calcium chloride, and 0.5 mM DTT)."

As defined herein, "RNA 5' polyphosphatase" or "RNA polyphosphatase" means an enzyme composition that is capable of digesting RNA that has a 5' polyphosphate group (e.g., primary RNA or RNA that has a 5' diphosphate group) to RNA that has a 5' monophosphate group under conditions wherein said RNA polyphosphatase does not digest capped RNA to RNA that has 5' monophosphate group. For example, in some embodiments an RNA 5' polyphosphatase is selected from among *Escherichia coli* RNA 5' polyphosphatase I (*E. coli* RPP I) and *Shigella* RNA 5' polyphosphatase I (*Shigella* RPP I), as described herein. However, with respect to a method of the invention, the enzyme can be any enzyme from any source that has RNA 5' polyphosphatase activity in the particular method. For example, baculovirus phosphatase (BVP) (Takagi, T. et al., Proc. Natl. Acad. Sci. USA 95: 9808-9812, 1998; Gross, C. H. and Shuman, S., J. Virology 72: 7057-7063, 1998), human PIR1 protein (Deshpande, T. et al., J. Biol. Chem. 274: 16590-16594, 1999), and *E. coli* RppH protein (Deana, A et al., Nature 451: 355-358, 2008) have been reported to convert 5'-triphosphorylated RNA to 5'-monophosphorylated RNA, but their activities on capped RNA have not been investigated or reported. It is contemplated that this activity will be tested. In some embodiments of the methods of the present invention, any of the proteins, selected from among BVP, PIR1, and RppH protein, that does not have activity in converting capped RNA to RNA that has a 5' monophosphate group is used as the RNA polyphosphatase.

Although RNA polyphosphatase is defined herein with respect to its capability of digesting a 5' polyphosphate group (e.g., a 5' triphosphate group of a primary RNA) to a 5' monophosphate group, RNA polyphosphatase can also have other enzymatic activities. For example, it will be understood herein that RNA polyphosphatase can also remove phosphates from any linear polyphosphate comprising two or more phosphates that is joined to the 5' end of an RNA molecule. In addition, RNA polyphosphatase may also be capable of digesting a linear polyphosphate comprising two or more phosphates that is joined to the 5' end of DNA, a ribonucleotide, a deoxyribonucleotide, or even a non-nucleic acid polyphosphate substrate.

The RNA polyphosphatase can be from a native protein or a recombinant protein. The term "native protein" is used herein to indicate a protein isolated from a naturally occurring (i.e., a nonrecombinant) source. The term "recombinant protein" or "recombinant polypeptide" as used herein refers to a protein molecule expressed from a recombinant DNA molecule. Molecular biological techniques may be used to produce a recombinant form of a protein with identical or similar properties as compared to the native form of the protein. Variants of the native sequence may also be made to, for example, improve expression, purification, or other desired properties of the polypeptide.

The RNA polyphosphatase that is a recombinant protein can be a fusion protein. As used herein, the term "fusion protein" refers to a chimeric protein containing the protein of interest (e.g., the RNA polyphosphatase or fragments thereof) joined to an exogenous protein fragment (e.g., the fusion partner which contains a non-RNA polyphosphatase protein). The fusion partner may enhance the solubility of RNA polyphosphatase protein as expressed in a host cell, may provide an affinity tag to allow purification of the recombinant fusion protein from the host cell or culture supernatant, or both. If desired, the fusion protein may be removed from the protein of interest (e.g., RNA polyphosphatase or fragments thereof) by a variety of enzymatic or chemical means known to the art.

In preferred embodiments of the present invention, the RNA polyphosphatase composition comprises a purified protein. As used herein, the term "purified" or "to purify" means the result of any process that removes some of a contaminant from the component of interest, such as a protein. For example, a particular desired protein (e.g., RNA polyphosphatase) is purified by removal of other contaminating undesired proteins, nucleic acid, carbohydrate, lipid and/or small biochemical molecules. The removal of contaminants results in an increase in the percentage of desired protein in the composition. For example, in preferred embodiments, the RNA polyphosphatase composition is purified so as to be free of contaminating nucleic acids and enzymes with activity on nucleic acids.

In some preferred embodiments, the RNA polyphosphatase is obtained by expression of an *Escherichia coli* RNA polyphosphatase gene (and/or functional variants and homologues thereof) in a plasmid or other vector that is replicated and expressed in *Escherichia coli* cells, since RNA polyphosphatase obtained from such a recombinant source is of a higher purity, free from contaminating enzymatic activities, and generally at a higher enzyme concentration than is obtained from non-recombinant sources.

The term "gene" as used herein, refers to a DNA sequence that comprises control and coding sequences necessary for the production of the encoded polypeptide or protein precursor (e.g., RNA polyphosphatase). The polypeptide can be encoded by a full-length coding sequence or by any portion of the coding sequence, as long as the desired protein activity is retained.

In preferred embodiments of the invention, the RNA polyphosphatase is "stabilized", by which we mean that the RNA polyphosphatase is sufficiently pure of proteases and other contaminants which contribute to degradation and loss of enzyme activity and is provided in a formulation of enzyme storage buffer in which there is no significant loss of activity during storage at −20 degrees C. for at least six months. One suitable enzyme storage buffer for providing a stabilized RNA polyphosphatase comprises a 50% glycerol solution containing 50 mM Tris-HCl (pH 7.5), 100 mM NaCl, 100 mM EDTA, 1 mM DTT and 0.1% of the non-ionic detergent Triton X-100. One form of the *E. coli* purified enzyme was found to be approximately a 19-kDa protein. Another form of the *E. coli* purified enzyme was found to be approximately a 24-kDa protein. The nucleic acid sequence (SEQ ID NO: 1) and amino acid sequence (SEQ ID NO: 2) of *E. coli* RNA polyphosphatase variants were determined (FIG. 2). It was also found that *Shigella* contains RNA polyphosphatase proteins that exhibit identical sequences to those found in *E. coli*. The term "RNA polyphosphatase", as used herein, can refer to the variants of the protein or to the gene, unless indicated otherwise.

Moreover, variant forms of RNA polyphosphatase are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of RNA polyphosphatase disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry, pg.* 17-21, 2nd ed, WH Freeman and Co., 1981). It can be readily determined whether a change in the amino acid sequence of a peptide results in a functional polypeptide by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

Variants may be produced by methods such as directed evolution or other techniques for producing combinatorial libraries of variants, described in more detail below. In still other embodiments of the present invention, the nucleotide sequences of the present invention may be engineered in order to alter an RNA polyphosphatase coding sequence including alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.). In some embodiments, a variant nucleic acid sequence encodes a native protein sequence, because of the degeneracy of the genetic code. In some embodiments, variants are provided to select optimal codons for a particular recombinant expression system of interest.

Still other embodiments of the present invention provide mutant or variant forms of RNA polyphosphatase. It is possible to modify the structure of a peptide having an activity of RNA polyphosphatase for such purposes as enhancing activity, or stability (e.g., ex vivo shelf life, and/or resistance to proteolytic degradation in vivo). Such modified peptides are considered functional equivalents of peptides having an activity of the subject RNA polyphosphatase proteins as defined herein. A modified peptide can be produced in which the amino acid sequence has been altered, such as by amino acid substitution, deletion (including truncations), or addition.

Moreover, as described above, variant forms (e.g., mutants) of the subject RNA polyphosphatase proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present RNA polyphosphatase proteins, as well as truncation mutants, and is especially useful for identifying variant sequences (i.e., mutants) that are functional in RNA polyphosphatase activity. The purpose of screening such combinatorial libraries is to generate, for example, novel RNA polyphosphatase variants that have improved or altered RNA polyphosphatase activity.

Therefore, in some embodiments of the present invention, RNA polyphosphatase variants are engineered by the present method to provide altered (e.g., increased or decreased) RNA polyphosphatase activity. In other embodiments, RNA polyphosphatase variants are engineered to provide heat-stable (i.e., "thermostable") or heat-labile RNA polyphosphatase activity for particular applications. In other embodiments of the present invention, combinatorially-derived variants are generated which have substrate variability different than that of a naturally occurring RNA polyphosphatase. Such proteins, when expressed from recombinant DNA constructs, find use in the methods described herein.

Still other embodiments of the present invention provide RNA polyphosphatase variants that have intracellular half-lives different than the corresponding wild-type protein. For example, the altered protein can be rendered either more stable or less stable to proteolytic degradation or other cellular process that result in destruction of, or otherwise inactivate RNA polyphosphatase. Such variants, and the genes which encode them, can be utilized to alter the location of RNA polyphosphatase expression by modulating the half-life of the protein. For instance, a short half-life can give rise to more transient RNA polyphosphatase biological effects and, when part of an inducible expression system, can allow tighter control of RNA polyphosphatase levels within the cell.

In still other embodiments of the present invention, RNA polyphosphatase variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of RNA polyphosphatase homologs, variants or other related proteins are aligned, preferably to promote the highest homology possible. Such a population of variants can include, for example, RNA polyphosphatase homologs from one or more species or sub-species, or RNA polyphosphatase variants from the same species or sub-species but which differ due to mutation or polymorphisms. Amino acids that appear at each position of the aligned sequences are selected to create a degenerate set of combinatorial sequences.

In a preferred embodiment of the present invention, the combinatorial RNA polyphosphatase library is produced by way of a degenerate library of genes encoding a library of polypeptides which each include at least a portion of potential RNA polyphosphatase protein sequences. For example, a mixture of synthetic oligonucleotides can be enzymatically ligated into gene sequences such that the degenerate set of potential RNA polyphosphatase sequences are expressible as individual polypeptides, or alternatively, as a set of larger fusion proteins (e.g., for phage display) containing the set of RNA polyphosphatase sequences therein.

There are many ways by which the library of potential RNA polyphosphatase homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential RNA polyphosphatase sequences. The synthesis of degenerate oligonucleotides is well known in the art (See e.g., Narang, Tetrahedron Lett., 39: 39, 1983; Itakura et al., Recombinant DNA, in Walton (ed.), Proceedings of the 3rd Cleveland Symposium on Macromolecules, Elsevier, Amsterdam, pp 273-289, 1981; Itakura et al., Annu. Rev. Biochem., 53: 323, 1984; Itakura et al., Science 198: 1056, 1984; Ike et al., Nucl. Acid Res., 11: 477, 1983). Such techniques have been employed in the directed evolution of other proteins (See e.g., Scott et al., Science 249: 386, 1980; Roberts et al., Proc. Natl. Acad. Sci. USA 89: 2429, 1992; Devlin et al., Science 249: 404, 1990; Cwirla et al., Proc. Natl. Acad. Sci. USA 87: 6378, 1990; as well as U.S. Pat. Nos. 5,223,409; 5,198,346; and 5096815).

It is contemplated that RNA polyphosphatase nucleic acids (e.g., SEQ ID NO: 1, and fragments and variants and homologs thereof) can be utilized as starting nucleic acids for directed evolution. These techniques can be utilized to develop RNA polyphosphatase variants having desirable properties such as increased, decreased, or altered RNA polyphosphatase activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458, 1996; Eckert and Kunkel, PCR Methods Appl., 1: 17-24, 1991; Caldwell and Joyce, PCR Methods Appl., 2: 28, 1992; and Zhao and Arnold, Nuc. Acids Res. 25: 1307, 1997). After mutagenesis, the resulting clones are selected for desirable activity (e.g., screened for RNA polyphosphatase activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324, 1994; U.S. Pat. Nos. 5,837,458; 5,830,721; 5,811,238; 5,733, 731). Gene shuffling involves random fragmentation of several mutant DNAs followed by their reassembly by PCR into full length molecules. Examples of various gene shuffling procedures include assembly following DNase treatment, the staggered extension process, and random priming in vitro recombination. In the DNase-mediated method, DNA segments isolated from a pool of positive mutants are cleaved into random fragments with DNase I and subjected to multiple rounds of PCR with no added primer. The lengths of random fragments approach that of the uncleaved segment as the PCR cycles proceed, resulting in mutations present in different clones becoming mixed and accumulating in some of the resulting sequences. Multiple cycles of selection and shuffling have led to the functional enhancement of several enzymes (Stemmer, Nature, 370:398, 1994; Stemmer, Proc. Natl. Acad. Sci. USA, 91: 10747, 1994; Crameri et al., Nat. Biotech., 14: 315, 1996; Zhang et al., Proc. Natl. Acad. Sci. USA, 94: 4504, 1997; and Crameri et al., Nat. Biotech., 15: 436, 1997).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of RNA polyphosphatase homologs or variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Fragments of the nucleic acids and proteins of the present invention may also be used, so long as the fragments encode or possess the desired enzymatic activity.

The enzymatic activity of RNA polyphosphatase can be defined in various ways using different substrates (e.g., an NTP, a primary RNA, or 6,8-difluoro-4-methylumbelliferyl phosphate), conditions, and assays. For example, one unit definition that can be used is: "one unit of RNA polyphosphatase is the amount of enzyme that releases one nanomole of inorganic phosphate from ATP in 60 minutes at 37° C. under standard reaction assay conditions (e.g., using 1 mM ATP in a reaction buffer consisting of 50 mM HEPES/KOH, pH 7.5, 0.1 M NaCl, 1 mM EDTA, 0.1% BME and 0.01% TRITON X100)."

The terms "sample" and "biological sample" are used in their broadest sense and encompass samples or specimens obtained from any source including biological and environmental sources. As used herein, the term "sample" when used to refer to biological samples obtained from organisms, includes fluids, solids, tissues, and gases. In preferred embodiments of this invention, biological samples include bodily fluids, isolated cells, fixed cells, cell lysates and the like. For example, in some embodiments, the sample is a formalin-fixed paraffin-embedded (FFPE) tissue section, and the RNA contained in the sample comprises degraded RNA molecules, including degraded capped RNA, degraded RNA that has a 5' polyphosphate group, degraded RNA that has a 5' monophosphate group, and/or degraded RNA that has a 5' hydroxyl group. Thus, in some embodiments of any of the methods for obtaining, isolating, purifying, or quantifying one or more RNA molecules, the sample contains degraded RNA, and the method is used for obtaining, isolating, purifying, or quantifying the respective degraded RNA (e.g., degraded capped RNA or degraded 5'-triphosphorylated RNA) in the sample. In some of these embodiments, the one or more RNA molecules that are obtained, isolated, purified, or quantified comprise only or predominantly the 5' end portions of RNA molecules derived from the naturally occurring undegraded RNA molecules (e.g., only the 5' end portions of capped RNA molecules or of 5'-triphosphorylated RNA molecules). However, these examples are not to be construed as limiting the types of samples that find use with the present invention. In some embodiments, the sample contains RNA that has been amplified (e.g., using any of the RNA amplification reactions known in the art). In general, at least one step of such RNA amplification reactions comprises in vitro transcription of double-stranded cDNA prepared from pre-existing RNA in the sample.

"Transcription" means the formation or synthesis of an RNA molecule by an RNA polymerase using a DNA molecule as a template. The invention is not limited with respect to the RNA polymerase that is used for transcription. For example, in some embodiments, a T7-type RNA polymerase is used.

A "T7-type RNA polymerase" as defined herein is a wild-type or mutant form of an RNA polymerase derived from a T7-type bacteriophage, including both phage-encoded enzymes and enzymes obtained by cloning the RNA polymerase gene in a DNA vector and expressing it in a bacterial or other cell. This is based on the fact that the genetic organization of all T7-type bacteriophage that have been examined has been found to be essentially the same as that of T7. Examples of T7-type bacteriophages include *Escherichia coli* phages T3, phi I, phi II, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 (Hausmann, Current Topics in Microbiology and Immunology 75: 77-109, 1976; Korsten et al., J. Gen. Virol. 43: 57-73, 1975; Dunn, et al., Nature New Biology 230: 94-96, 1971; Towle, et al., J. Biol. Chem. 250: 1723-1733, 1975; Butler and Chamberlin, J. Biol. Chem. 257:5772-5778, 1982). Mutant T7-type RNAPs (e.g., as described in Sousa et al., U.S. Pat. No. 5,849,546; Padilla, R and Sousa, R, Nucleic Acids Res., 15: e138, 2002; Sousa, R and Mukherjee, S, Prog Nucleic Acid Res Mol. Biol., 73: 1-41, 2003), such as T7 RNAP Y639F mutant enzyme, T3 RNAP Y640F mutant enzyme, SP6 RNAP Y631F mutant enzyme, T7 RNAP having altered amino acids at both positions 639 and 784, T3 RNAP having altered amino acids at both positions 640 and 785, or SP6 RNAP having altered amino acids at both positions 631 and 779 can also be used in some embodiments of methods or assays of the invention. In particular, such mutant enzymes can corporate dNTPs and 2'-F-dNTPs (e.g., using a T7 R&DNA™ polymerase or a DURASCRIBE™ T7 transcription kit, EPICENTRE), in addition to ddNTPs and certain other substrates, which are advantageous for synthesis of RNA molecules with specific properties and uses. In some embodiments, phage N4 mini-vRNAP (which is a transcriptionally active 1,106-amino acid domain of the N4 vRNAP, which corresponds to amino acids 998-2103 of N4 vRNAP that has certain domains in common with T7-type RNAPs; Kazmierczak, K. M., et al., EMBO J. 21: 5815-5823, 2002; U.S. Pat. No. 7,452,705) is used as the T7-type RNA polymerase. Alternatively, in some embodiments, the N4 mini-vRNAP Y678F mutant enzyme that can incorporate non-canonical nucleotides such as 2'-F-dNTPs (U.S. Pat. No. 7,452,705) is used as the T7-type RNA polymerase. In order to carry out transcription, an RNA polymerase recognizes and binds to a DNA sequence of approximately 25 nucleotides in length called an "RNA polymerase promoter," a "transcription promoter" or simply a "promoter," and initiates transcription therefrom. In most cases, the promoter sequence is double-stranded. As used herein, the strand of a double-stranded promoter that is covalently joined to the template strand for synthesis of RNA is defined as the "sense strand" or "sense promoter sequence" and its complement is defined as the "anti-sense strand" or the "anti-sense promoter sequence."

EXAMPLES

The following examples serve to illustrate certain preferred embodiments and aspects of the present invention and are not to be construed as limiting the scope thereof.

Discovery and Purification of RNA Polyphosphatase

The discovery of an RNA polyphosphatase (RPP) occurred when we renatured *Escherichia coli* proteins in situ in SDS-PAGE gels. The SDS-PAGE (15%) running gel was prepared by polymerization of the polyacrylamide in the presence of gamma $^{32}$P-end-labeled RNA (synthesized by in vitro transcription of a linear DNA template using T7 RNA polymerase, T7 reaction buffer, gamma-$^{32}$P-labelled GTP, and unlabelled ATP, CTP and UTP). After electrophoresis, the SDS-PAGE running buffer was exchanged by incubating the gel in non-SDS-containing buffer to remove the SDS and permit protein renaturation in situ. The gel was incubated in buffer overnight and the gel was stained with SYBR Gold (Invitrogen, Carlsbad, Calif.). An unstained band was evident which migrated with a molecular weight of approximately 30,000. However, when the gel was fixed in 7.5% acetic acid and then dried and subjected to autoradiography, two bands devoid of radioactivity were observed which migrated with molecular weights of approximately 30,000 (30 kDa) and approximately 19,000 (19 kDa). SYBR Gold staining indicated the presence of RNA in the 19-kDa band, consistent with dephosphorylation, but not with degradation, of $^{32}$P-end-labeled RNA by the 19-kDa protein. The lack of SYBR Gold staining in the 30-kDa band was consistent with the protein in the band being an RNase, which was likely RNase I.

In order to simplify the assay for enzyme activity and facilitate purification of the enzyme, we searched for alternative enzyme substrates. We found that the fluorogenic phosphatase substrate 6,8-difluoro-4-methylumbelliferyl phosphate (DiFMUP) was a substrate for the 19-kDa protein. Upon hydrolysis, this substrate is converted to the fluorescent product 6,8-difluoro-7-hydroxy-4-methylcoumarin (DiFMU), which has an absorption peak at 358 nm and an emission peak at 455 nm. Surprisingly, the RPP enzyme exhibited greater than 50-fold more activity using DiFMUP as a substrate than using 4-methylumbelliferyl phosphate (4MUP) as a substrate. Thus, using a standard ultraviolet transilluminator, DiFMUP was used to detect a single 19-kDa fluorescent band in total extracts of *Escherichia coli* after protein renaturation in situ on a polyacrylamide gel. The band also was stained by Coomassie blue protein dye. Using the simpler DiFMUP assay, we were able to scale up purification of the RNA polyphosphatase protein and further characterize its physical and enzymatic properties. For example, in some embodiments, the RNA polyphosphatase activity is purified using one or more of the following methods: polyethyleneimine fractionation; ammonium sulfate fractionation; Bio-Rex 70 cation exchange column chromatography (e.g., Bio-Rex 70 chromatography); gel filtration column chromatography (e.g., Sephacryl S100); and anion exchange column chromatography (e.g., SP-Sepharose). The RNA polyphosphatase activity chromatographed as a single peak in both ion exchange and gel filtration columns, suggesting that the 19-kDa protein was the sole enzyme showing this activity.

Identification of the Gene Coding for RNA Polyphosphatase

To identify the protein and determine the genetic locus coding for the RNA polyphosphatase enzyme, the RNA polyphosphatase was digested in-gel with trypsin, and the resulting tryptic digests were analyzed using matrix-assisted laser desorption ionization time of flight mass spectrometry (MALDI-TOF MS). When compared with protein sequences in NCBI database using the MASCOT search engine, the tryptic peptide sequences derived from RNA polyphosphatase matched with a protein from *Escherichia coli* 53638. In fact the top twelve matches (protein scores ranging from 439 to 229, p<0.05) were to the same protein in the database from different strains of *Escherichia coli*. An alignment of the twelve proteins from different strains of *Escherichia coli* showed that they were essentially identical. In *Escherichia coli* K12 (MG1655), this protein (locus tag b2252) has been annotated as an aluminum-inducible protein of unknown function. The corresponding aluminum-inducible (ais) gene maps to 50.04 min and codes for approximately a 200-amino-acid protein. It is classified as a non-essential gene whose mRNA levels were induced 16 fold after addition of 0.2 mM $ZnSO_4$ to a culture grown in a defined medium lacking inorganic phosphate. Information on the protein product of this gene was not available since it has not been detected before. Without being bound by theory, the search for conserved domains in the ORF indicates that the protein could be a member of the phosphoglycerate mutase-like superfamily. Catalytic activity of enzymes in this family typically involves phosphorylation of histidine.

Cloning and Over-Expression of the ais Gene

We amplified the ais gene (b2252 locus) by polymerase chain reaction using genomic DNA isolated from *Escherichia coli* K12 (MG1655) using specific oligonucleotide primers that contain recognition sites for NdeI and BamHI restriction enzymes. The forward primer containing the NdeI recognition sequence was engineered to change the first codon GTG to ATG. The amplified product was cloned into the corresponding sites of an inducible T7-based pET plasmid expression vector, and following transformation of competent *Escherichia coli* EC100 cells and selection of recombinants, the sequence of the insert DNA was verified to be that of ais gene. RNA polyphosphatase activity of the protein from the recombinant clone was detected by fluorescence using the in situ gel assay as before and over-expression of the protein upon induction was monitored by Coomassie blue staining. Purified native RNA polyphosphatase was used as a control in these experiments. Less total protein from the recombinant clone was used for the gel assay in order to minimize detection of the endogenous RNA polyphosphatase present in the uninduced cells.

Two fluorescent and Coomassie blue-staining bands were seen in protein extracts prepared from induced recombinant cells. One of these bands from the induced recombinant cells was a soluble protein with RNA polyphosphatase activity that was identical in size and properties to the 19-kDa native RNA polyphosphatase enzyme. In addition, a second 24-kDa protein with RNA polyphosphatase activity, which was present predominantly in inclusion bodies, was also over-expressed in the induced recombinant cells. The amino terminus of the purified native enzyme and recombinant 24-kDa and 19-kDa RNA polyphosphatase enzymes were determined by Edman degradation. The sequences of the amino terminus of the native and the over-expressed recombinant 19-kDa protein, S-N-G-L-P, were identical. The amino terminus of the 24-kDa recombinant protein, M-L-A-F, corresponds to the amino terminus of cloned ais gene. The amino terminal sequence, S-N-G-L-P, of the native enzyme suggested that perhaps the protein is processed by a signal peptidase and the mature enzyme is present in the periplasmic space. To determine the sub-cellular distribution of the native enzyme, *Escherichia coli* B cells were converted to spheroplasts and the RNA polyphosphatase activity that was released into the supernatant (periplasmic fraction) and that was retained by the spheroplast (cytoplasmic fraction) was measured by fluorescence in situ gel assay. RNA polyphosphatase was detected in the periplasmic fraction and this activity co-migrated with the 19-kDa size of the purified native enzyme. The cytoplasmic fraction also contained RNA polyphosphatase activity that migrated as a 19-kDa protein but no 24-kDa RNA polyphosphatase was detected. Without being bound by theory, the data suggests that the recombinant 19-kDa RNA polyphosphatase is a periplasmic protein derived from the 24-kDa protein by processing of the amino terminal end. The presence of a 19-kDa RNA polyphosphatase activity observed in the cytoplasmic fraction of non-recombinant cells could have been due to incomplete conversion of cells into spheroplasts and the presence of the 24-kDa active protein in recombinant cells was probably due to unprocessed protein that was present in inclusion bodies within the recombinant cells. It is interesting to note that the ais gene was categorized as a secreted protein by Zalucki, Y M, et al. (Nucleic Acids Res. 35: 5748-5754, 2007) but the predicted cleavage site was different from the identified amino terminus.

Catalytic Properties of Purified RNA Polyphosphatase

The purified RNA polyphosphatase enzyme is active over a wide range of pH (e.g., it has optimal activity in the range between pH 5.0 and pH 8.0). Surprisingly, and in contrast to some other phosphate-removing enzymes, it does not require a divalent cation like $Mg^{2+}$ and is active in the presence of EDTA. In fact, the enzyme was inhibited in the presence of 1 mM $Mg^{2+}$ cations.

In addition to removing the beta and gamma phosphates from nucleic acids, such as primary RNA or from 5'-diphosphorylated RNA (e.g., from a capping enzyme RNA triphosphatase reaction), the purified ~19-kDa single-subunit RNA polyphosphatase can remove phosphate groups from a variety of other substrates, including nucleoside-5'-diphosphates and triphosphates (e.g., NTPs, NDPs, dNTPs, dNDPs). The product of hydrolysis is a nucleoside 5' monophosphate and inorganic orthophosphate. Nucleoside-5'-monophosphates are not substrates. ADP was hydrolyzed at 50% efficiency compared to ATP. The enzyme hydrolyzes nucleoside triphosphates in a stepwise manner, releasing inorganic orthophosphate instead of pyrophosphate. A time course analysis of products of ATP hydrolysis by thin layer chromatography showed accumulation of ADP first followed by appearance of AMP. Interestingly, while polyphosphate was as good a substrate for RNA polyphosphatase as ATP, inorganic pyrophosphate does not appear to be a substrate. The symmetrical dinucleoside triphosphate G[5']ppp[5']G and its methylated derivative m7G[5']ppp[5']G were hydrolyzed very poorly, if at all, suggesting that the enzyme is an exopolyphosphatase. Also, while DiFMUP, the substrate used in the initial screening and identification of the enzyme was a good substrate, 4-methyl-umbelliferyl phosphate and p-nitrophenyl phosphate (PNPP) were poor substrates for the enzyme, and bis (p-nitrophenyl) phosphate was hydrolyzed very poorly. Without being bound by theory, it is postulated that the fluorines at positions 6 and 8 probably play a role in making DiFMUP a substrate for the enzyme even though it has a single phosphate. 5-Bromo-4-chloro-3-indolyl phosphate and the phosphoamino acid phosphoserine were essentially not recognized at all as substrates.

We believe that RNA polyphosphatases that can cleave RNA that has a triphosphate or diphosphate group on its 5' end to a monophosphate, but that cannot cleave capped RNA to a monophosphate have not previously been described in the art. This activity is useful for a variety of methods described herein. However, without being bound by theory, we do not believe that the bacteria from which RNA polyphosphatase is derived use the enzyme for a similar function in nature. Rather, we believe that the finding that RNA polyphosphatase is a periplasmic enzyme in prokaryotes indicates that its natural function may be for scavenging for essential nutrients (e.g., phosphate) in its environment. Thus, the methods described herein may be artificial, even if convenient for our purposes. Nevertheless, since these and some other phosphatases are multifunctional and are active on a broad range of phosphorylated compounds (e.g., nucleotides, sugar phosphates, phospholipids, and polyphosphates), the roles played by RNA polyphosphatases in nature remains unknown.

Example of a Kit and Method for Obtaining, Isolating, or Purifying Capped RNA from a Mixture of Capped and Uncapped RNA or Quantifying the Percentage of Capped RNA in a Mixture of Capped and Uncapped RNA A. Kit Contents The following compositions and kit comprise or consist of:
 1. RNA 5' Polyphosphatase @ 2 U/µl
 2. Terminator™ 5'-Phosphate-Dependent Exonuclease @ 1 U/µl
 3. 10× Enzyme Reaction Buffer:
  41.5% (500 mM Tris-HCl, pH 8.0, 20 mM $MgCl_2$ and 1 M NaCl), and 58.5% (0.5 M HEPES-KOH, pH 7.5, 1 M NaCl, 10 mM EDTA, 1% β-mercaptoethanol and 0.1% Triton X-100).
 4. RNase-Free Water Storage Buffers: Both RNA 5' Polyphosphatase and Terminator Exonuclease are supplied in a 50% glycerol solution containing 50 mM Tris-HCl (pH 7.5), 0.1 M NaCl, 0.1 mM EDTA, 1 mM dithiothreitol, and 0.1% Triton® X-100.

Activity and Unit Definitions: 1 Unit of RNA Polyphosphatase results in the release of one nanomole of inorganic phosphate from ATP in 1 hour at 37° C. under standard assay conditions. 1 U of Terminator Exonuclease digests 0.1 µg of rRNA substrate into acid-soluble nucleotides in 1 hour at 30° C. under standard assay conditions.

Storage: Store at −20° C. in a freezer without a defrost cycle.

RNA Quantification: In some embodiments, the Quant-iT™ RiboGreen® RNA Reagent/Kit (Molecular Probes®/Invitrogen™) is used for RNA quantification.

B. Method or Assay for Isolating or Quantifying the Percentage of Capped RNA in a Mixture of Capped and Uncapped RNA Background:

The RNA 5' Polyphosphatase in the kit selectively digests RNA that has a 5' triphosphate group to RNA that has a 5' monophosphate group, but does not digest capped RNA in the sample. Then, the Terminator™ 5'-Phosphate-Dependent Exonuclease selectively digests the RNA that has a 5' monophosphate group to RNA mononucleotides, but does not digest capped RNA. If desired, the capped RNA in the sample is quantified and the percentage of capped RNA in the sample is calculated by comparing it to the initial quantity of RNA prior to treatments with the RNA 5' Polyphosphatase and the Terminator™ 5'-Phosphate-Dependent Exonuclease.

Samples or solutions that contain a mixture of capped and uncapped RNA can be from any source, including from a biological sample that contains purified total RNA from cell or mixture of cells, or from an in vitro capping reaction. In some embodiments, the RNA from an in vitro capping reaction is from a co-transcriptional capping reaction (e.g., using the MESSAGEMAX™ T7 ARCA capped message transcription kit, EPICENTRE). In some embodiments, the RNA from an in vitro capping reaction is from a post-transcriptional capping reaction using a capping enzyme system (e.g., using the mSCRIPT™ mRNA production system or the SCRIPT-CAP™ capping enzyme; EPICENTRE).

Protocol for the Method or Assay

The protocol below uses samples containing 4 μg of RNA, but the reaction can be scaled up or down depending on user needs and RNA availability using the same ratios of enzyme to micrograms of RNA given below. The control, which is run in parallel, consists of the same sample that is not treated with RNA 5' Polyphosphatase or Terminator™ 5'-Phosphate-Dependent Exonuclease.

Step 1. Provide a sample containing 8 μg of RNA purified from a biological sample or from a co-transcriptional or post-transcriptional capping reaction, and divide the sample into two 4 μg-containing aliquots. Label one aliquot as "Control" (untreated) and the other as "Experimental" (treated).

Step 2. Combine the following reaction components in the order given:

For the Experimental Reaction

| | |
|---|---|
| x μl | RNase-Free Water |
| 5 μl | 10X Enzyme Reaction Buffer |
| 1 μl | ScriptGuard ™ RNase Inhibitor (40 U/μl) (EPICENTRE) (optional, not provided in the kit) |
| y μl | Sample containing 4 μg of RNA |
| 1 μl | RNA 5' Polyphosphatase (2 U/μl) |
| 1 μl | Terminator 5'-Phosphate-Dependent Exonuclease (1 U/μl) |
| 50 μl | Total reaction volume |

For the Control Reaction

| | |
|---|---|
| x μl | RNase-Free Water |
| 5 μl | 10X Enzyme Reaction Buffer |
| 1 μl | ScriptGuard ™ RNase Inhibitor (40 U/μl) (EPICENTRE) (optional, not provided in the kit) |
| y μl | Sample containing 4 μg of RNA |
| 50 μl | Total reaction volume |

Step 3. Incubate at 37° C. for 30 minutes.
Step 4. Stop the reactions by placing on dry ice.
Step 5. If desired, quantify the RNA in each tube. For example, using the Quant-iT RiboGreen RNA Reagent/Kit (Molecular Probes/Invitrogen), follow the manufacturer's recommendations to construct a standard curve over a range of 0-200 ng (0-1000 ng/ml). Individually, take 5 μl from each reaction above and add it to 195 μl of TE buffer consisting of 10 mM Tris-HCl (pH 7.5) and 1 mM EDTA. Use 40 μl of this mixture in the RiboGreen assay. This is equivalent to 80 ng of RNA if the capping reaction is 100% efficient. All reactions should be done, minimally, in duplicate.

$$\text{The Percentage Capped } RNA = \frac{\text{The quantity of } RNA \text{ in the Experimental Reaction}}{\text{The quantity of } RNA \text{ in the Control Reaction}} \times 100$$

Accuracy was +/−10% or better using the Quant-iT RiboGreen RNA Reagent/Kit.

Note: Magnesium ($Mg^{++}$) is inhibitory to RNA 5' Polyphosphatase activity. Care should be taken to purify the RNA so it does not contain $Mg^{++}$ from previous reactions (e.g., from co-transcriptional or post-transcriptional capping reactions).

All publications and patents mentioned in the present application are herein incorporated by reference. Modification or variation of the described methods and compositions will be apparent to those skilled in the art without departing from the scope and spirit of the invention. Although the invention has been described in connection with specific preferred embodiments, it will be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for obtaining, isolating, or purifying capped RNA in a sample that contains said capped RNA and at least one uncapped RNA, the method comprising the steps of:

(1) providing: (i) a sample that contains capped RNA and at least one uncapped RNA that has a 5' triphosphate group or a 5' diphosphate group, (ii) an RNA polyphosphatase that is active in the presence of EDTA and is inhibited in the presence of 1 mM or greater $Mg^{2+}$, and (iii) a 5' exoribonuclease;

(2) contacting the sample with the RNA polyphosphatase thereby forming a first reaction mixture such that the RNA that has a 5' triphosphate group or a 5' diphosphate group is converted to RNA that has a 5' monophosphate group in said first reaction mixture; and (3) contacting said first reaction mixture with said 5' exoribonuclease under conditions such that said RNA that has a 5' monophosphate group in said first reaction mixture is digested by the 5' exoribonuclease, but said capped RNA in said first reaction mixture is not digested by the 5' exoribonuclease, thereby obtaining, isolating, or purifying said capped RNA.

2. The method of claim 1, wherein said RNA polyphosphatase is *E. coli* 5'-RNA Polyphosphatase (*E. coli* RPP I) or *Shigella* 5'-polyphosphatase I (Shigella RPP I), and said contacting the sample with the RNA polyphosphatase is performed in the absence of $Mg^{2+}$.

3. The method of claim 1, further comprising transforming an eukaryotic cell with the capped RNA that is obtained, isolated, or purified from step (3).

4. The method of claim 1, wherein said eukaryotic cell is an antigen-presenting cell (APC) selected from the group consisting of: a dendritic cell, a macrophage, an epithelial cell, and an artificial APC.

5. The method of claim 1, wherein the capped RNA is from a biological sample or is from an in vitro capping reaction selected from the group consisting of: (i) a co-transcriptional capping reaction comprising an RNA polymerase and a dinucleotide cap analog, and (ii) a post-transcriptional capping reaction that employs a capping enzyme system comprising RNA guanyltransferase enzymatic activity.

6. The method of claim 1, wherein the capped RNA comprises bacterial mRNA that is capped in vitro using a capping enzyme system comprising RNA guanyltransferase enzymatic activity.

7. The method of claim 1, further comprising: prior to step (2), quantifying the amount of total RNA in the sample; and step (4), after step (3), comprising:

(i) quantifying the amount of RNA that is not digested by the 5' exoribonuclease in step (3), thereby quantifying the amount of said capped RNA in the sample; and/or (ii) quantifying the amount of RNA that is digested by the 5' exoribonuclease in step (3), thereby quantifying the amount of said uncapped RNA in the sample.

8. The method of claim 7, wherein the sample provided in step (1) additionally comprises RNA that has a 5' monophosphate group and the method further comprises quantifying the amount of said RNA that has a 5' monophosphate group in the sample, wherein, prior to step (2), the method additionally comprises the sub-steps of:

contacting the sample provided in step (1) with the 5' exoribonuclease under conditions such that RNA in the sample that has a 5' monophosphate group is digested by the 5' exoribonuclease but said capped RNA and said uncapped RNA that has a 5' triphosphate group or a 5' diphosphate group is not digested by the 5' exoribonuclease, and quantifying the amount of RNA that is digested by the 5' exoribonuclease or the amount of RNA that is not digested by the 5' exoribonuclease in the sample, whereby the amount of RNA in the sample that is digested by the 5' exoribonuclease in the sub-steps indicates the amount of RNA that has a 5' monophosphate group in the sample.

9. The method of claim 7, wherein the sample provided in step (1) additionally comprises RNA that has a 5' hydroxyl group, wherein the method additionally comprises providing a polynucleotide kinase and ATP in step (1), and the method further comprises the steps of:

(5) contacting the sample from step (1) with the polynucleotide kinase and the ATP under conditions for sufficient time and forming a second reaction mixture, wherein said RNA that has a 5' hydroxyl group is phosphorylated to RNA that has a 5' monophosphate group in said second reaction mixture;

(6) contacting said second reaction mixture with the 5' exoribonuclease under conditions such that said RNA that has a 5' monophosphate group is digested by the 5' exoribonuclease, but said capped RNA and said uncapped RNA that has a 5' triphosphate group or a 5' diphosphate group are not digested by the 5' exoribonuclease; and (7) quantifying the amount of RNA that is digested by the 5' exoribonuclease or the amount of RNA that is not digested by the 5' exoribonuclease in step (6), whereby the amount of RNA in the sample that is digested by the 5' exoribonuclease in step (6) indicates the amount of RNA that has a 5' hydroxyl group in the sample.

* * * * *

SEQUENCE LISTING

<160> NUMBER OF SEQ ID NOS: 6

<210> SEQ ID NO 1
<211> LENGTH: 603
<212> TYPE: DNA
<213> ORGANISM: Escherichia coli

<400> SEQUENCE: 1

```
atgttagctt tttgccgctc ttcgttgaag tcaaaaaaat atatcatcat tttactggcg      60
ctcgctgcaa ttgccggact gggtactcat gccgcctgga gtagcaatgg tttgccacgt     120
atcgacaata aaacactggc cagactggca cagcagcacc cggttgtcgt tttgtttcgt     180
catgctgaac gttgcgaccg ttcaaccaat caatgcttgt cagataaaac aggtattacg     240
gttaaaggta cccaggatgc ccgtgaactg ggcaacgctt ttagtgctga tatccctgat     300
ttcgatcttt attccagtaa taccgtccgg accattcagt cggctacctg gttttcagcg     360
ggtaaaaaat tgacggtaga taaacgactt cttcagtgcg gtaatgagat ttatagtgca     420
```

```
attaaggact tacaaagcaa agcgcctgat aaaaatatcg ttattttcac ccataatcat    480
tgcctgacat atattgctaa agataagcgt gacgcgacat ttaaacctga ttatctggat    540
ggtttagtca tgcatgtgga aaaaggcaaa gtttatctgg atggggaatt cgttaaccac    600
taa                                                                  603

<210> SEQ ID NO 2
<211> LENGTH: 200
<212> TYPE: PRT
<213> ORGANISM: Escherichia coli

<400> SEQUENCE: 2

Met Leu Ala Phe Cys Arg Ser Ser Leu Lys Ser Lys Tyr Ile Ile
1               5                   10                  15

Ile Leu Leu Ala Leu Ala Ala Ile Ala Gly Leu Gly Thr His Ala Ala
            20                  25                  30

Trp Ser Ser Asn Gly Leu Pro Arg Ile Asp Asn Lys Thr Leu Ala Arg
                35                  40                  45

Leu Ala Gln Gln His Pro Val Val Leu Phe Arg His Ala Glu Arg
    50                  55                  60

Cys Asp Arg Ser Thr Asn Gln Cys Leu Ser Asp Lys Thr Gly Ile Thr
65                  70                  75                  80

Val Lys Gly Thr Gln Asp Ala Arg Glu Leu Gly Asn Ala Phe Ser Ala
                85                  90                  95

Asp Ile Pro Asp Phe Asp Leu Tyr Ser Ser Asn Thr Val Arg Thr Ile
                100                 105                 110

Gln Ser Ala Thr Trp Phe Ser Ala Gly Lys Lys Leu Thr Val Asp Lys
            115                 120                 125

Arg Leu Leu Gln Cys Gly Asn Glu Ile Tyr Ser Ala Ile Lys Asp Leu
        130                 135                 140

Gln Ser Lys Ala Pro Asp Lys Asn Ile Val Ile Phe Thr His Asn His
145                 150                 155                 160

Cys Leu Thr Tyr Ile Ala Lys Asp Lys Arg Asp Ala Thr Phe Lys Pro
                165                 170                 175

Asp Tyr Leu Asp Gly Leu Val Met His Val Glu Lys Gly Lys Val Tyr
            180                 185                 190

Leu Asp Gly Glu Phe Val Asn His
        195                 200

<210> SEQ ID NO 3
<211> LENGTH: 4
<212> TYPE: PRT
<213> ORGANISM: Escherichia coli

<400> SEQUENCE: 3

Met Leu Ala Phe
1

<210> SEQ ID NO 4
<211> LENGTH: 4
<212> TYPE: PRT
<213> ORGANISM: Escherichia coli

<400> SEQUENCE: 4

Ser Asn Gly Leu
1
```

```
<210> SEQ ID NO 5
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (8)..(14)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa is Leu, Val, or Ile
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: Xaa is Leu, Val, or Ile

<400> SEQUENCE: 5

Gly Xaa Xaa Xaa Xaa Xaa Glu Xaa Xaa Xaa Xaa Xaa Xaa Xaa Arg Glu
1               5                   10                  15

Xaa Xaa Glu Glu Xaa Gly Xaa
            20

<210> SEQ ID NO 6
<211> LENGTH: 5
<212> TYPE: PRT
<213> ORGANISM: Escherichia coli

<400> SEQUENCE: 6

Ser Asn Gly Leu Pro
1               5
```